United States Patent
Shehada et al.

[11] Patent Number: 6,124,597
[45] Date of Patent: Sep. 26, 2000

[54] METHOD AND DEVICES FOR LASER INDUCED FLUORESCENCE ATTENUATION SPECTROSCOPY

[75] Inventors: Ramez E. N. Shehada, Los Angeles; Vasilis Z. Marmarelis, Irvine; Warren S. Grundfest, Los Angeles, all of Calif.

[73] Assignee: Cedars-Sinai Medical Center, Los Angeles, Calif.

[21] Appl. No.: 08/889,017

[22] Filed: Jul. 7, 1997

[51] Int. Cl.[7] .................................................. G01N 21/64
[52] U.S. Cl. .................................. 250/461.2; 250/458.1; 600/321; 600/320; 600/323; 356/342
[58] Field of Search .......................... 250/461.2, 458.1; 600/321, 320, 323; 356/342

[56] References Cited

U.S. PATENT DOCUMENTS

| | | |
|---|---|---|
| 4,641,650 | 2/1987 | Mok . |
| 4,675,529 | 6/1987 | Kushida . |
| 4,707,131 | 11/1987 | Schiek . |
| 4,753,530 | 6/1988 | Knight et al. . |
| 4,786,813 | 11/1988 | Svanberg et al. . |
| 4,945,245 | 7/1990 | Levin . |
| 4,957,114 | 9/1990 | Zeng et al. . |
| 5,122,974 | 6/1992 | Chance . |
| 5,341,805 | 8/1994 | Stavridi et al. . |
| 5,452,723 | 9/1995 | Wu et al. . |
| 5,456,252 | 10/1995 | Vari et al. . |
| 5,495,850 | 3/1996 | Zuckerman . |
| 5,507,287 | 4/1996 | Palcic et al. . |
| 5,635,402 | 6/1997 | Alfano ........................................ 436/63 |
| 5,760,406 | 6/1998 | Powers ................................. 250/461.2 |

FOREIGN PATENT DOCUMENTS

| | | |
|---|---|---|
| 0 703 445 A2 | 9/1995 | European Pat. Off. . |
| WO 89/12223 | 6/1989 | WIPO . |
| WO 97/08538 | 8/1996 | WIPO . |

*Primary Examiner*—Constantine Hannaher
*Assistant Examiner*—Andrew Israel
*Attorney, Agent, or Firm*—Pretty, Schroeder & Poplawski

[57] ABSTRACT

The Laser Induced Fluorescence Attenuation Spectroscopy (LIFAS) method and apparatus preferably include a source adapted to emit radiation that is directed at a sample volume in a sample to produce return light from the sample, such return light including modulated return light resulting from modulation by the sample, a first sensor, displaced by a first distance from the sample volume for monitoring the return light and generating a first signal indicative of the intensity of return light, a second sensor, displaced by a second distance from the sample volume, for monitoring the return light and generating a second signal indicative of the intensity of return light, and a processor associated with the first sensor and the second sensor and adapted to process the first and second signals so as to determine the modulation of the sample. The methods and devices of the inventions are particularly well-suited for determining the wavelength-dependent attenuation of a sample and using the attenuation to restore the intrinsic laser induced fluorescence of the sample. In turn, the attenuation and intrinsic laser induced fluorescence can be used to determined a characteristic of interest, such as the ischemic or hypoxic condition of biological tissue.

54 Claims, 17 Drawing Sheets

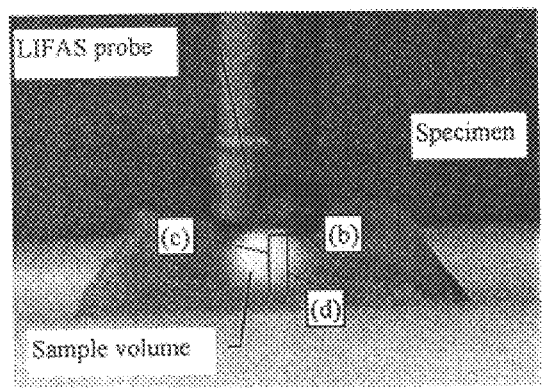
(a)
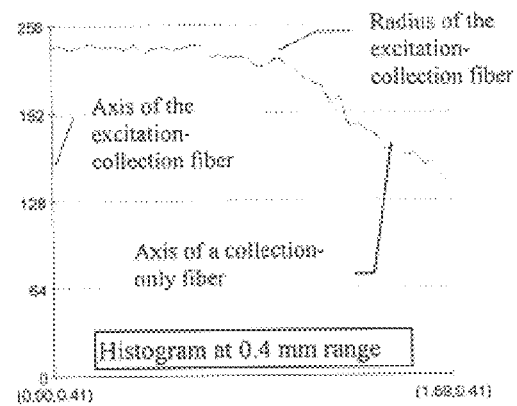
(b)
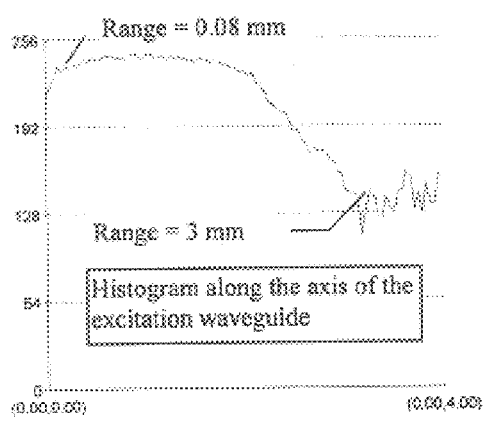
(c)
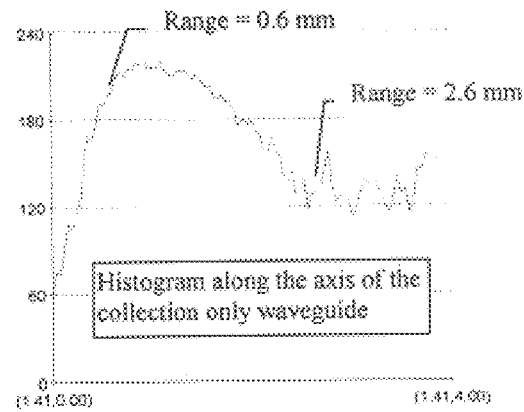
(d)
FIG. 12

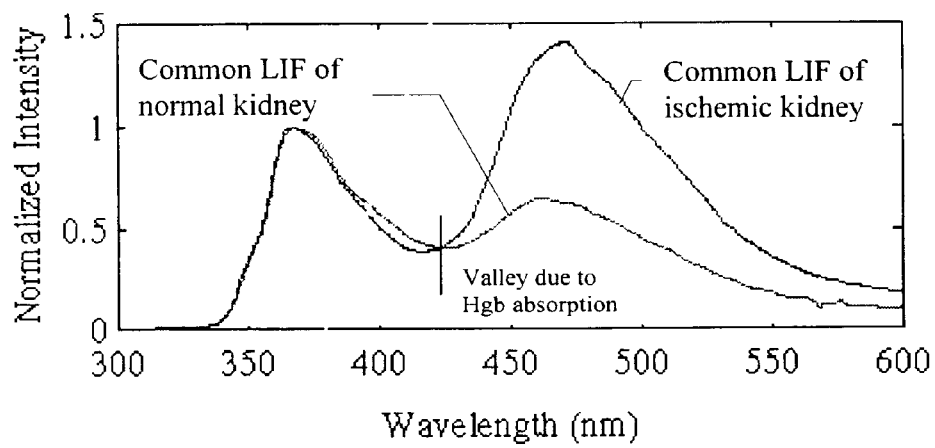
(a)
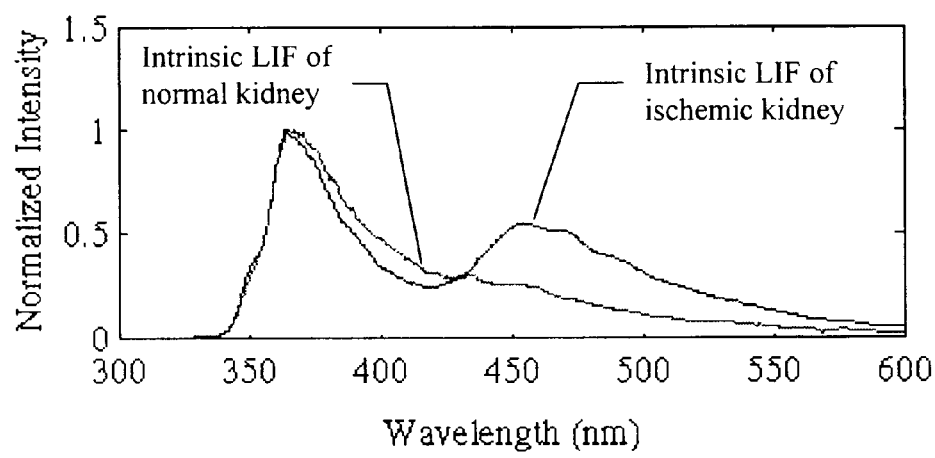
(b)
FIG. 14

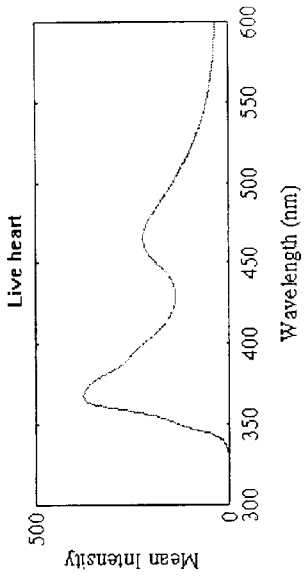
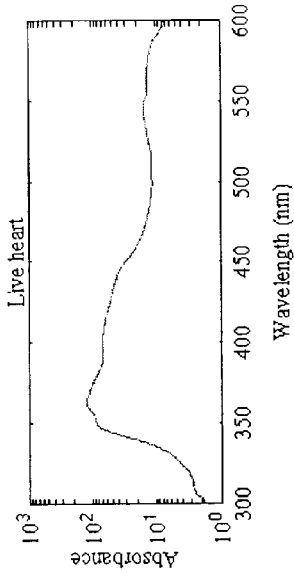
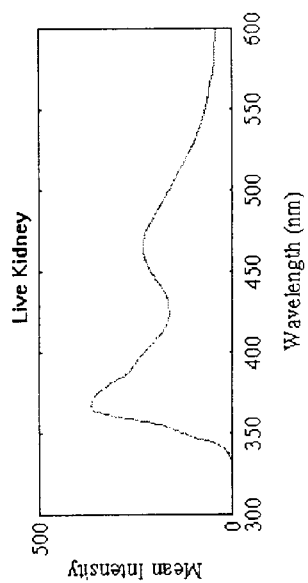
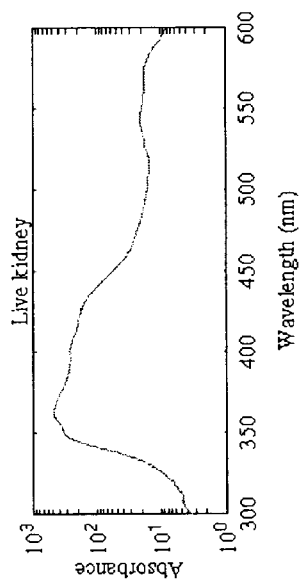
FIG. 17

METHOD AND DEVICES FOR LASER INDUCED FLUORESCENCE ATTENUATION SPECTROSCOPY

BACKGROUND OF THE INVENTION

The present invention is directed to methods and devices for determining a spectroscopic characteristic of a sample utilizing laser induced fluorescence attenuation spectroscopy ("LIFAS"). More particularly, the invention is directed to methods and devices for measurement of the wavelength-dependent attenuation of the sample and subsequent restoration of the intrinsic laser induced fluorescence ("LIF") for physiological monitoring, biological tissue characterization and biochemical analysis.

Conventionally, samples have been characterized by determining the attenuation and laser induced fluorescence ("LIF"). Once the attenuation and LIF of a sample have been determined, these spectroscopic properties can be utilized to determine a physical or physiological property of the sample. For example, the attenuation of a sample can be used to determine the concentrations of mixture components or turbidity of a fluid. Similarly, the LIF of a sample has been used in fields such as analytical chemistry, environmental monitoring, industrial inspection and medical diagnosis. In the medical field, for example, LIF spectroscopic techniques have been used for tissue characterization, malignant tumor identification, atherosclerotic plaque diagnosis, metabolism evaluation, and the like.

Conventionally, the attenuation or the absorption of a sample is determined by placing the sample between a light source and a detector and measuring any reduction in the intensity of the light as it passes through the sample. In order to obtain a measurement having an acceptable signal-to-noise ratio using these conventional techniques, it is important to transmit the incident light with sufficient intensity. Thus, the thickness of the sample and the wavelength of the incident light are important factors affecting the reliability of the resulting measurement. Moreover, because it is necessary to place the sample between the light source and the detector, it is difficult to perform attenuation measurements on certain types of samples, such as living tissue.

More recently, fiber optic techniques have been developed for the measurement of attenuation in which an optical fiber is used to guide the incident light to illuminate a sample inside a small chamber at the tip of a probe. A reflector is placed on the opposite side of the chamber to reflect the incident light into a second fiber which is associated with a detector. Unfortunately, these techniques find limited application with materials, such as fluids, that can readily pass into the chamber in the tip of the probe.

Conventionally, laser induced fluorescence ("LIFS") spectroscopic techniques utilize various optical configurations in which a laser is directed at a sample using an optical fiber and the LIF from the sample is collected using a second optical fiber. Alternatively, the same fiber can be used for excitation of the sample and the collection of LIF. In either case, the LIF collected by the fiber is modulated by the sample, e.g. by the wavelength-dependent absorption and scattering of constituents of the sample. Therefore, existing LIFS methods are limited by the fact that the "intrinsic" or "true" fluorescence of the sample's fluorophores cannot be determined. Recent reports have suggested measuring the diffuse reflectance spectrum of the tissue as a means for correcting the intrinsic LIF using Monte-Carlo mathematical formulations. However, such correction methods are critically dependent on the backscattering characteristics of the tissue. Furthermore, backscattering does not account for the effects of absorption and scattering suffered by the intrinsic fluorescence prior to its measurement.

In biological LIF techniques, lasers are used to cause fluorophores in the sample to emit fluorescence. The main fluorophores in normal biological tissue are tryptophan, collagen and elastin. Other fluorophores, such as NAD (nicotinamide adenine dinucleotide) and FAD (flavin adenine dinucleotide), are also normally present, but at much lower concentrations. Under certain conditions, the contribution of the various fluorophores to the LIF can change. For example, during an ischemic or hypoxic event, the tissue is deprived of oxygen and anaerobic respiration takes place. Consequently, the weak fluorophore NAD will be converted into the strong fluorophore reduced nicotinamide adenine dinucleotide ("NADH"). As a result, the LIF collected from the sample will reflect an increased contribution from NADH. This change is typically observed as a rise in the intensity of the LIF spectrum in the region of peak NADH emission, from about 470 to 490 nm. Thus, the metabolic state of the tissue can be determined by measuring the relative change in LIF intensity at the wavelength of peak NADH emission as compared to the relative change of the LIF intensity of fluorophores that are normally present in the tissue, such as elastin or collagen.

Unfortunately, the LIF of biological tissue is heavily modulated in the 390–450 nm range by the peak absorption of the main tissue chromophore, hemoglobin. Thus, although the intrinsic LIF spectra of normal tissue should approximately resemble that of the pure fluorophore components of the tissue, the measured LIF spectra has a valley in the 400–450 nm region that is associated with the hemoglobin absorption. As a result, the measured LIF spectrum tissue appears to have a double peak instead of the single peak spectrum associated with the pure fluorophores of the tissue. Hence, the LIF spectrum of normal tissue begins to resemble the spectrum associated with tissue suffering hypoxia or ischemia, which makes it more difficult to identify tissue abnormalities.

Furthermore, since the optical properties of biological tissue are influenced by its hemoglobin concentration, the measured LIF will vary with the level of blood perfusion throughout the cardiac cycle. The LIF of contractile tissue, such as the myocardium, is highly dependent on its state of contraction. Contraction increases the concentration of the fluorophore NADH and, hence, its contribution to tissue fluorescence. During contraction, however, blood is pumped out of the tissue, thereby reducing its hemoglobin concentration and, hence, light attenuation. Thus, a contracted myocardium retains less blood (i.e., a lower hemoglobin concentration) and, therefore, exhibits lower light absorption, than when relaxed.

Organs such as the brain, heart and kidney are the most sensitive to oxygen deficiency and can suffer permanent damage following an ischemic or hypoxic event. During open-heart surgery, for example, continuous monitoring of kidney perfusion, i.e., ischemia, is required. Similarly, since the success of a transplantation surgery is highly dependent on the level of organ perfusion at harvest and during preservation of the tissue, continuous monitoring of the organ is typically required.

Ischemia and hypoxia are both conditions that deprive tissue of oxygen, leading to anaerobic metabolism and the accumulation of the metabolic coenzyme NADH. The coenzyme NADH is a fluorescent molecule. Therefore, ischemia and hypoxia can be indirectly detected using LIF techniques by sensing increased concentrations of NADH and interpreting its elevation as a sign of oxygen deficiency. A common indicator of oxygen deficiency is the ratio between the LIF intensity at wavelengths associated with the peak fluorescence emission of NADH, collagen and elastin. However, such methods have not been practically applied for the detection of ischemia because of several complications. First, these methods cannot determine whether the elevated NADH concentration is caused by ischemia, hypoxia or hypermetabolism. Second, scarred or fibrosed tissue would be detected as normal because of their low NADH concentration. Finally, the indicator ratios are calculated by normalizing the intensity of NADH peak fluorescence by that of collagen or elastin. Although the fluorescence of the structural proteins elastin and collagen does not vary with tissue oxygenation, their fluorescence vary with the site of measurement.

The intrinsic LIF of biological tissue has a single peak spectral profile resembling that of the pure structural proteins which are primarily elastin and collagen. However, this single peak profile is modulated by the attenuation of hemoglobin, especially about 410 nm, to yield a distorted, double-peak spectrum. The second spurious peak at about 470 nm results from the spectral valley created by heavy hemoglobin absorption at about 410 nm. Unfortunately, this second peak overlaps and obscures the peak fluorescence emission of NADH at about 470–490 nm, which may impede ischemia detection techniques that are based on NADH concentration.

The methods and devices of the present invention will enable measurement of several LIF parameters that directly relate to the state of tissue perfusion and/or hemoglobin oxygenation. This offers superior accuracy over the currently available LIF techniques which detect ischemia and hypoxia indirectly by sensing an upsurge in NADH fluorescence. In particular, the methods and devices of the present invention can directly indicate the presence and the level of hypoxia or ischemia. Furthermore, the methods of the present invention utilize novel criteria for discrimination between normal and ischemic or hypoxic tissue.

It is readily apparent that existing LIFS techniques in medicine and industry are affected by modulations of the intrinsic LIF. Thus, there is need for methods and devices for determining the intrinsic laser induced fluorescence while eliminating or minimizing modulating influences in order to provide more accurate and complete characterization of a sample. In particular, there is a need for method and devices for characterization of biological tissue. The present invention addresses these and other needs.

SUMMARY OF THE INVENTION

The present invention is embodied in a system and related method for laser-induced fluorescence attenuation spectroscopy ("LIFAS") in which the attenuation and intrinsic LIF of a sample can be determined. The LIFAS system employs a source, a first sensor, a second sensor and a processor. The source, preferably a laser, emits light to irradiate a sample volume in a sample so that the sample volume produces return light, which preferably includes laser induced fluorescence. The first sensor monitors the return light at a first distance from the sample volume and generates a plurality of signals representing the intensity of the return light in predetermined wavelength bands. The second sensor monitors the return light at a second distance from the sample volume and generates a plurality of signals representing the intensity of the return light, preferably over the same wavelength bands. Where the first and second distances are different, the processor can be used to determine the wavelength-dependent attenuation of the sample using the signals of both sensors. The measured attenuation will typically reflect the effects of both absorption and scattering by the sample. For maximum signal-to-noise ratio, it is preferred that the first and second detectors monitor return light from the sample volume at a location in proximity to the sample volume.

Once the wavelength-dependent light attenuation is determined, the attenuation can be used to restore the intrinsic LIF of the fluorophores of the sample. Once the attenuation and intrinsic fluorescence have been determined, these factors can be used in a variety of applications, including medical diagnosis. In the preferred embodiment, the attenuation and fluorescence are used for the detection of ischemia and hypoxia of biological tissue. Ischemia and hypoxia are detected by monitoring spectral changes in the intrinsic LIF to detect a rise in the concentration of NADH in the tissue. Since ischemia is caused by a decrease in the blood content of the tissue, ischemic tissue will have lower concentrations of hemoglobin. Consequently, in ischemic tissue, absorption by hemoglobin, especially in the 390–450 nm spectral band, will be reduced. Changes in the wavelength of peak light transmission, especially in the 450–500 nm band, can also be used to detect hemoglobin oxygenation and, hence, the presence of hypoxia or ischemia. Finally, multicriteria associative memories (MAM) can be used as an attenuation or fluorescence spectral classifier.

Other features and advantages of the present invention will be apparent from the following description of the preferred embodiments, taken in conjunction with the accompanying drawings, which illustrate, by way of example, the principles of the invention.

BRIEF DESCRIPTION OF THE DRAWINGS

FIG. 12 is a graph of the attenuation spectrum measured from normal and ischemic renal cortex of rabbit kidney using LIFAS devices and methods in accordance with the invention;

FIG. 14 is a graph of the intensity $I_{co}(\lambda)^c$ of the signal measured by a collection-only waveguide from normal, hyperoxic and hypoxic tissue;

FIGS. 17(a)–(b) are graphs of the mean LIF intensity of live kidney and heart tissue and FIGS. 17(c)–(d) are the corresponding LIFAS-derived attenuation spectra.

DESCRIPTION OF THE PREFERRED EMBODIMENTS

Figure 1:
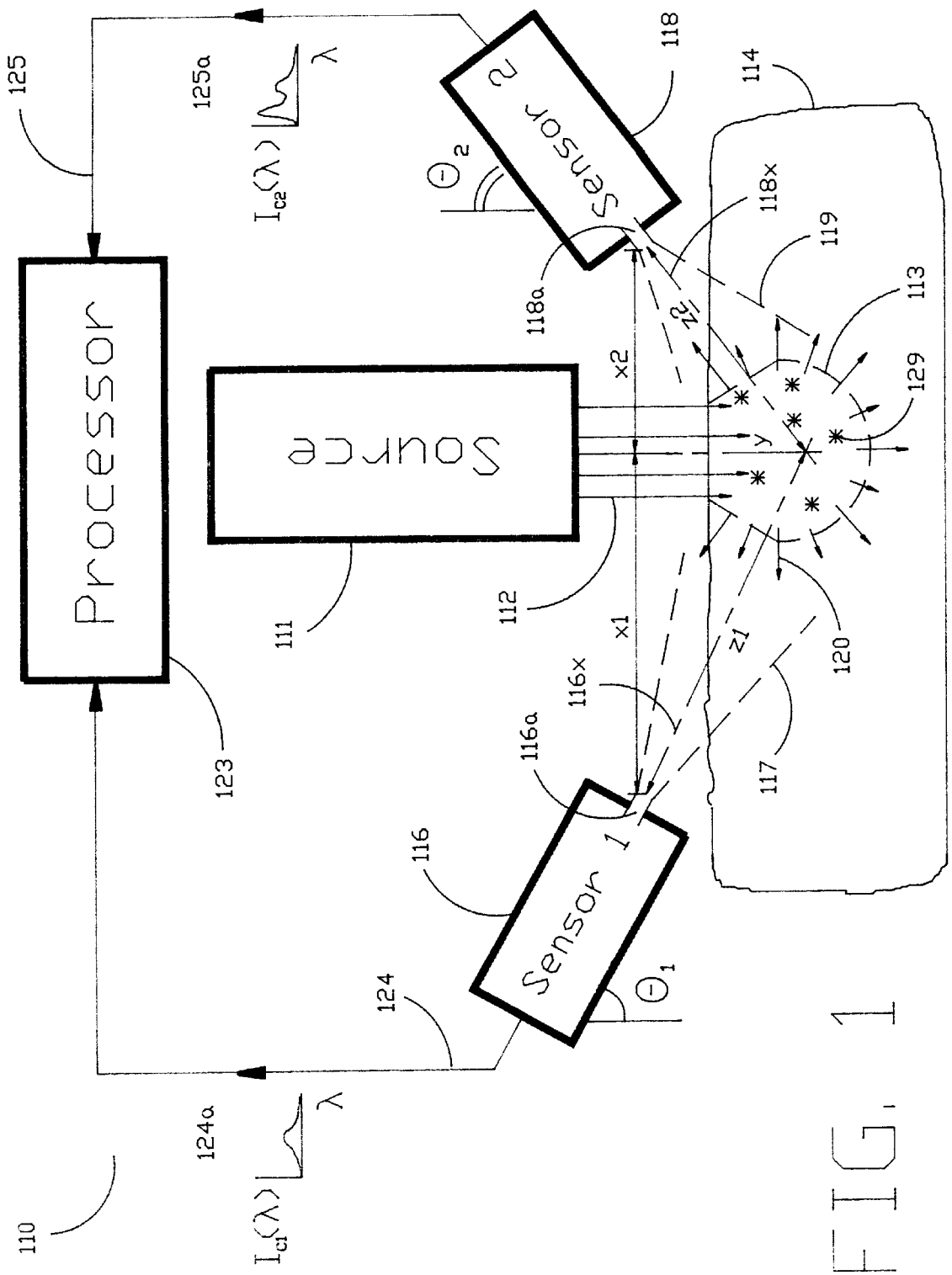
FIG. 1 is a schematic diagram of a spectroscopic system in accordance with the invention.

As shown in the exemplary drawings and, in particular, FIG. 1 thereof, the present invention is embodied in a spectroscopic system 110 and related method for measuring the attenuation and/or optical rotation caused by a sample 114. The spectroscopic system 110 shown in FIG. 1, includes a source 111 that produces radiation 112, which is directed at a sample volume 113 within the sample 114. The source 111 is preferably a laser and the radiation 112 is preferably monochromatic ultraviolet (UV), visible or infrared (IR) radiation 112. Nevertheless, the source 111 can be selected to produce other types of radiation, such as broadband or polarized radiation, useful for a particular application. The spectroscopic system 110 further includes a first sensor 116 displaced by a distance Z1 from the sample volume 113, and a second sensor 118 displaced by a distance Z2 from the sample volume 113, which are used to monitor return radiation 120 from the sample 114. In the preferred embodiment, the return radiation 120 will include fluorescence of the fluorophores of the sample 114.

The sensors 116 and 118 each include an aperture 116a and 118a, respectively, through which the return radiation 120 is observed and collected. The sensors 116 and 118 typically can only observe the events occurring within the volume defined by a solid angle emerging from the aperture of the sensor. This volume is known as the numerical aperture or the field of view of the sensor. Thus, first and second sensors 116 and 118 include numerical apertures 117 and 119, respectively, that are adapted to receive a portion of the return radiation 120 from the sample 114. The sensors 116 and 118 can be tilted at different angles $\Theta_1$ and $\Theta_2$ and selected to have different numerical apertures 117 and 119 so that the sensors 116 and 118 can selectively monitor return radiation 120 from all or part of the sample volume 113.

The sensors 116 and 118 each generate a signal 124a and 125a, respectively, representing the intensity $I_{c1}(\lambda)$ and $I_{c2}(\lambda)$ and/or polarization of the return radiation 120. Preferably, the signals 124a and 125a are generated at a plurality of wavelengths within predetermined wavelength bands. The signal 124a from the first sensor 116 and the signal 125a from the second sensor 118 are communicated by signal paths 124 and 125, respectively, to a processor 123. As discussed in additional detail, below, the processor 123 processes the signals 124a and 125a to determine a spectral characteristic of interest, such as the attenuation and/or optical rotation of the return radiation 120 caused by the sample 114.

To determine the attenuation of the return radiation 120 caused by the sample, the sensors 116 and 118 are positioned at non-equivalent distances Z1 and Z2 from the sample volume 113. Preferably, the first and second sensors 116 and 118 will be positioned so that one of the sensors will be in the immediate proximity of the sample volume 113 while the other sensor is positioned at a location adjacent to the first sensor, but displaced slightly further from the sample volume 113. It has been found that this arrangement advantageously improves the signal-to-noise ratio and, hence, measurement accuracy of the spectroscopic system 110.

The attenuation of the return radiation 120 is dependent on the distance traveled by the return radiation 120 through the sample 114. Hence, the signal 124a measured by the first sensor 116 and the signal 125a measured by the second sensor 118 will suffer different attenuation where the distances Z1 and Z2 from the sample volume 113 are not equivalent. The processor 123 can be used to process the signals 124a and 125a to determine the wavelength-dependent attenuation of the sample 114. The attenuation determined by the spectroscopic system 110 will reflect the effects of light absorption and scattering by the sample 114. Where the radiation 112 causes fluorophores in the sample 114 to fluorescence, the attenuation of the sample 114 can be used to determine the intrinsic fluorescence 129 of the fluorophores in the sample volume 113. The methods by which the attenuation and intrinsic LIF are determined are discussed in detail below.

The source 111, shown in FIG. 1, can be any radiation source, such as a laser or a lamp emitting excitation radiation 112 at a wavelength capable of interacting with the sample 114. The sensors 116 and 118 will preferably include a detector, which can be as simple as individual light-sensitive diodes with appropriate band pass filters, or more complicated sensors such as an optical spectrum analyzer. Preferably, the sensor is a suitable spectrograph or spectrometer equipped with a suitable sensor. Alternatively, the sensor can include a multispectral CCD camera.

In the preferred embodiment, the source 111 is an XeCl excimer laser emitting monochromatic ultraviolet radiation at 308 nm. Each of the sensors 116 and 118 is a spectrograph (Model FF250, ARIES Inc., Concorde, Mass.) associated with a 1024 element intensified photo diode array (PDA) to image the resolved spectrum. Each PDA is connected to an optical multichannel analyzer (OMA III, EG&G Princeton Applied Research Corporation, Princeton, N.J.). The OMA reads the light spectrum imaged by the PDA to produce the signals 124a and 125a. A 335 nm longpass filter (Schott WG335) is placed in front of the aperture of each of the sensors 116 and 118 to remove any backscattered 308 nm excitation radiation. The processor 123 is a personal computer that is networked to each of the sensors 116 and 118 via the signal paths 124 and 125 to receive the signals 124a and 125a, respectively.

In other applications, such as measuring the optical rotation or anisotropy of a sample, it will be desirable to position the first and second sensors 116 and 118 at equivalent distances Z1 and Z2 from the sample volume 113. Optical rotation is observed in optically active materials. An optically active material is characterized by a lack of symmetry in its molecular or crystalline structure which causes a rotation of the plane of polarization in incident-plane-polarized radiation. The extent to which the plane of polarization is rotated will typically vary from one optically active material to another. In addition, the extent of rotation may depend on the number of molecules in the path of the radiation, the wavelength of the radiation, and the temperature of the material. Anisotropy, on the other hand, is caused by a selective response of the sample to radiation travelling in different directions. In certain biological samples, for example, anisotropy can result from microscopic inhomogeneity in the tissue structure. Use of equivalent distances Z1 and Z2 will minimize the contribution of the path-length-dependent attenuation to the overall attenuation measured by the system 110. Therefore, the optical rotation or anisotropy of the sample can be determined more easily.

The LIFA system 110 shown in FIG. 1 can be adapted to measure optical rotation by utilizing first and second sensors 116 and 118 which are adapted to measure the polarization-dependent intensity of the return radiation. In particular, the first sensor 116 can be adapted to measure a first optical angle $\phi_1$ (not shown) yielding the maximum intensity of the first portion of the return radiation 120. Meanwhile, the second sensor 118 can be adapted to measure a second optical angle $\phi_2$ (not shown) yielding the maximum intensity of the second portion of the return radiation 120. The optical rotation of the return light 120 will be given by the difference between the angles $\phi_1$ and $\phi_2$, provided that the system has been properly calibrated. The same sensor is used for determination of the attenuation of the sample will find utility for monitoring the optical rotation. These sensors can be adapted to such measurements by placing a rotatable polarizing filter at each of the apertures 116a and 118a of the first and second sensors 116 and 118, respectively.

Figure 2:
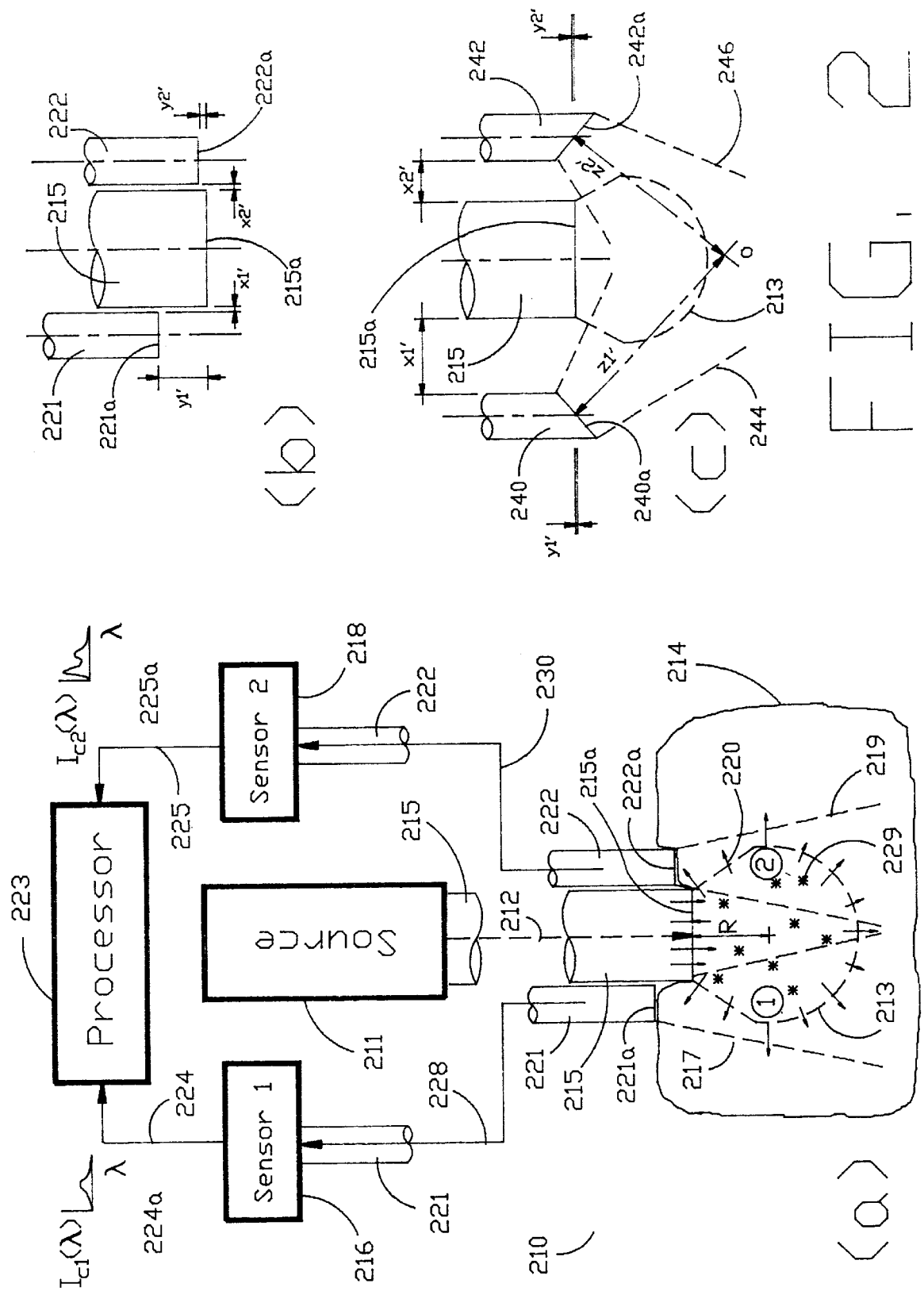
FIG. 2(a) is a schematic diagram of a Laser Induced Fluorescence Attenuation Spectroscopy system ("LIFAS") in accordance with the present invention having an excitation waveguide and a first and second collection waveguides.
FIG. 2(b) is a schematic diagram of an alternative configuration of the collection waveguides of FIG. 2(a)
FIG. 2(c) is a schematic diagram of yet another alternative configuration of the collection waveguides of FIG. 2(a)

An alternative embodiment of the present invention is shown in FIG. 2(a). In this embodiment, the spectroscopic system 110 of FIG. 1 has been adapted as a Laser Induced Fluorescence Attenuation Spectroscopy ("LIFAS") system 210. In the LIFAS system 210, a source 211 emits laser radiation 212 at an intensity and a wavelength capable of inducing fluorescence of the sample 214. The laser radiation 212 is transmitted through an excitation waveguide 215 to a sample volume 213 within the sample 214 where the laser radiation 212 excites local fluorophores in the sample volume 213 to emit intrinsic fluorescence 229. The intrinsic fluorescence 229 of the fluorophores in the sample volume 213 is modulated, for example, by the absorption and scattering of the local chromophores (not shown) and scatterers (not shown) present in the sample 214, respectively.

Two collection waveguides 221 and 222 having apertures 221a and 222a and numerical apertures 217 and 219 are disposed about the excitation waveguide 215. As shown in FIG. 2(b), the collection waveguides 221 and 222 may be positioned such that their apertures 221a and 222b are laterally displaced from the excitation waveguide 215 by the distances x1' and x2' and/or axially displaced from the aperture 215a of the excitation waveguide 215 by the distances y1' and y2'. Preferably, the lateral distances x1' and x2' are small or zero. Meanwhile, the axial distances y1' and y2' are preferably selected to be small and unequal, while one of the axial distances is preferably zero. Also, it is desirable to position the apertures 215a, 221a and 222a of the waveguides 215, 221 and 222 in close proximity to or in contact with the sample 214 during use of the LIFAS system 210, as shown in FIG. 2(a).

An alternative configuration of the collection waveguides is shown in FIG. 2(c). In this configuration, the axial distances y1' and y2' are both zero. Meanwhile, the lateral distances x1' and x2' are selected to be small and unequal. The apertures 240a and 242a of the waveguides 240 and 242 are oblique such that the fields of view 244 and 246 are directed toward the sample volume 213 and to advantageously encompass the bulk of the sample volume 213. As shown in FIG. 2(c), the distances z1' and z2' are directed along the respective axes of the numerical apertures 244 and 246 and extend from the surface of the apertures 240a and 242a to the point of intersection of the axes of the numerical apertures 244 and 246, respectively.

The collection waveguide 221 collects a first portion 228 of the return light 220 and transmits the first portion 228 of the return light 220 to a first sensor 216. The first sensor 216 generates a first signal 224a, representing the intensity $I_{c1}(\lambda)$ of the first portion 228 of the return light 220 at a plurality of wavelengths within predetermined wavelength bands. Similarly, the collection waveguide 222 collects a second portion 230 of the return light 220 and transmits the second portion 230 of the return light 220 to the second sensor 218. The second sensor 218 generates a second signal 225a representing the intensity $I_{c2}(\lambda)$ of the second portion 230 of the return light 220 at a plurality of wavelengths preferably within the same wavelengths bands monitored by the first sensor 216.

The processor 223 then processes the first and second signals 224a and 225a to determine the wavelength-dependent attenuation of the sample 214. As discussed in detail, below, once the attenuation is known, either of the signals 224a or 225a can be processed to minimize the effects of attenuation and determine the intrinsic LIF 229 of the fluorophores in the sample volume 213. Alternatively, if the sensors 216 and 218 are selected to monitor the polarization of the first portion 228 and the second portion 230 of the return light 220, the processor 223 can be used to determine the optical rotation of the return light 220 caused by the sample 214.

Preferably, the intensity and wavelength of the laser radiation 212 should be sufficient to create a sample volume 213 that is large enough to have some overlap with the numerical apertures 217 and 219 of the collection waveguides 221 and 222, respectively. The numerical apertures 217 and 219 can be selected to encompass all or parts of the sample volume 213. Furthermore, longpass filters are placed before the inputs of the sensors 216 and 218 to selectively block backscattered excitation radiation.

In the preferred embodiment, the source 211 is an Xe—Cl excimer laser emitting 308 nm ultraviolet excitation radiation 212. The waveguides 215, 221 and 222 are advantageously comprised of optical fibers or optical fiber bundles, which can be integrated into a probe for ease of use and durability. The optical bundle and fibers are made of fused silica which is transparent to ultraviolet radiation. Specifically, a 1.4 mm diameter optical bundle is used as the excitation waveguide 215 while the collection waveguides 221 and 222 are 0.4 mm optical fibers disposed about the excitation bundle. In the preferred probe embodiment, the lateral range x1' and x2' are equal to zero while the axial distance y1' is about 0.6 mm and the axial distance y2' is about zero. Furthermore, the probe may be configured within, for example, the shaft of a hypodermic needle, so that the in-vivo physiological or pathological properties of biological tissue can be determined.

In the preferred embodiment, each of the sensors 216 and 218 is a spectrograph (Model FF250, ARIES Inc., Concorde, Mass.) associated with a 1024 element intensified photo diode array (PDA). Each PDA is connected to an optical multichannel analyzer (OMA III, EG&G Princeton Applied Research Corporation, Princeton, N.J.) which measures the intensity of the light spectrum imaged by the PDA and produces the signals 224a and 225a. The processor 223 is a personal computer that is networked to each of the sensors 216 and 218 via the signal paths 224 and 225 to receive the signals 224a and 225a, respectively.

Figure 11:
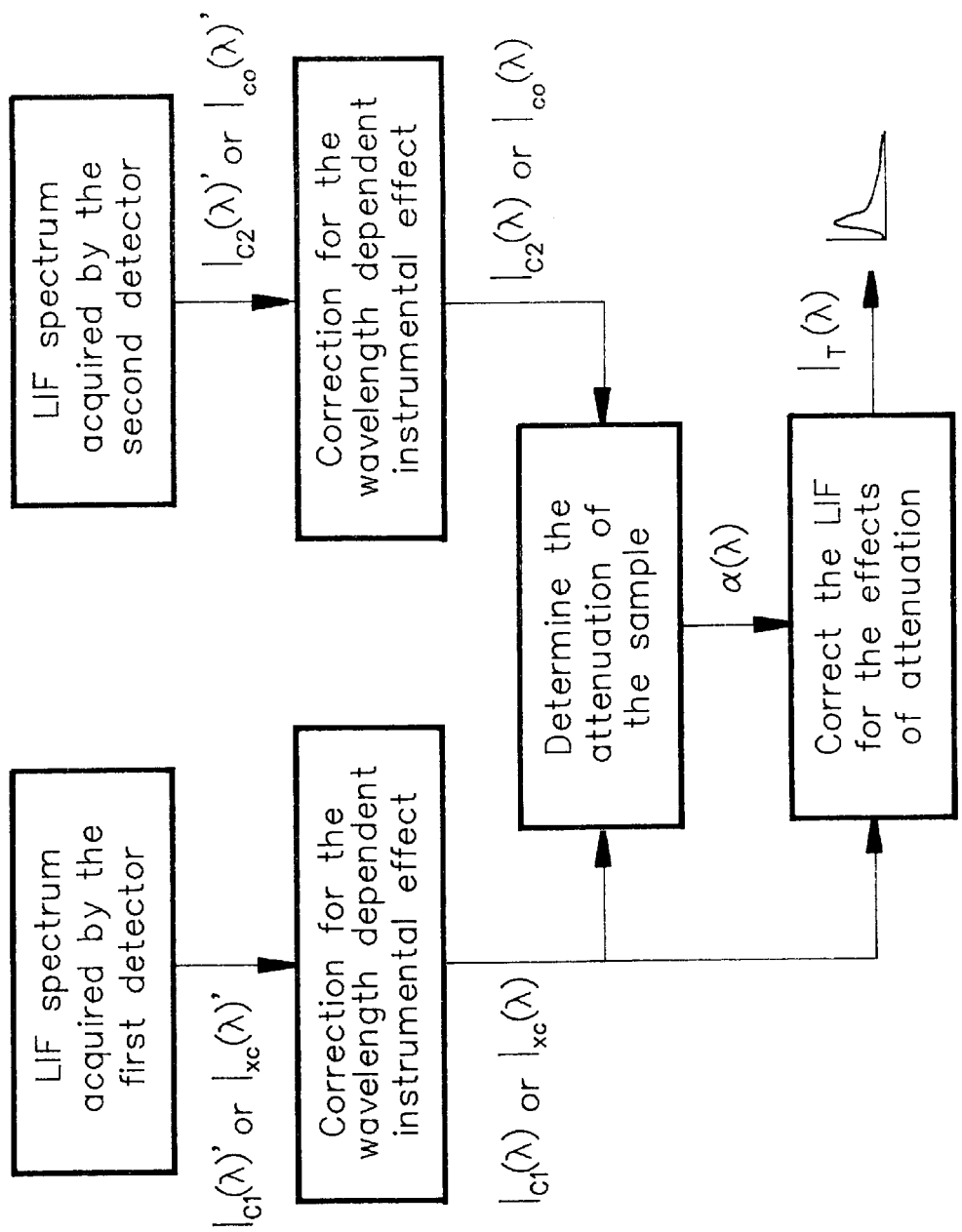
FIG. 11 is a block diagram of the method for determining the attenuation and the intrinsic fluorescence of a sample.

The method of determining the attenuation and intrinsic fluorescence of a sample is better understood with reference to the block diagram shown in FIG. 11, which illustrates the main steps involved in determining the wavelength-dependent attenuation coefficient $\alpha(\lambda)$ and the intrinsic fluorescence $I_I(\lambda)$ of a sample in accordance with the current invention. In the embodiment shown in FIG. 2(a), the first and second portions 228 and 230 of the return light 220 experience different attenuation effects due to the unequal path lengths traversed by the return light 220 from the sample volume 213 to the apertures 221a and 222a of the collection waveguides 221 and 222. The first portion 228 of the return light 220 collected by the aperture 221a travels an additional path-length of {y1'-y2'} through the tissue as compared to the second portion 230 of the return light 220 which is collected by the aperture 222a. Hence, the first portion 228 of the return light 220 suffers more path-length-dependent attenuation as compared to the second portion 230 of the return light 220. Thus, the signals 224a and 225a representing the intensity $I_{c1}(\lambda)$ and $I_{c2}(\lambda)$ at different wavelengths will exhibit differing levels of modulation caused by the attenuation of the sample 214.

In addition, the signals 224a and 225a will also exhibit wavelength-dependent modulations caused by the instrumental effects. The wavelength-dependent modulations due to the instrumental effects can be determined and, in turn, compensated for by conducting a calibration of the LIFAS system 210. System calibration can be performed using light from a standard lamp (Quartz Halogen Lamp, Model No. 63358, Oriel Instruments, Stratford, Conn.) having a predetermined continuous spectrum to measure the wavelength-dependent instrumental effects of the LIFAS system 210. Once these instrumental effects are known, the processor 223 can be adapted to correct the measured intensities $I_{c1}(\lambda)$ and $I_{c2}(\lambda)$ for modulations caused by the wavelength-dependent instrumental effects. The corrected intensities $I_{c1}(\lambda)^c$ and $I_{c2}(\lambda)^c$ representing the intensity of the first and second portions 228 and 230 of the return light 220 at different wavelengths can then used to determine the attenuation coefficient $\alpha(\lambda)$ of the sample 214 as described below.

The regions ① and ②, of FIG. 2(a) may be at an effective range, symbolized as "R," from which the collection waveguides 221 and 222 collect the majority of the first and second portions of return light 228 and 230, respectively. The effective range "R" will vary with the attenuation of the sample. However, the regions ① and ②, are geometrically symmetric with respect to the aperture 215a of the excitation waveguide 215 and, hence, have identical intensity of the intrinsic fluorescence 229 represented by $I_I(\lambda)$. Furthermore, since the lateral and axial distances x1', x2' and y1', y2' are predetermined by the configuration of the probe (in the preferred embodiment x1'=x2', y1'>y2', y2'≈0), the wavelength-dependent intensities $I_{c1}(\lambda)^c$ and $I_{c2}(\lambda)^c$ can be described by the following equations:

$$I_{c1}(\lambda)^c = I_I(\lambda) e^{-\alpha(\lambda) \cdot (R+y1')} \quad (1)$$

$$I_{c2}(\lambda)^c = I_I(\lambda) e^{-\alpha(\lambda) \cdot (R+y2')} \quad (2)$$

The attenuation coefficient $\alpha(\lambda)$ can be calculated independent of the value of "R" from (1) and (2) as follows:

$$\alpha(\lambda) = \{1/\{y2'-y1'\}\} \ln\{I_{c1}(\lambda)^c / I_{c2}(\lambda)^c\} \quad (3)$$

Where the difference {y2'-y1'} is a known constant, "e" is the natural exponential function and "ln" is the natural logarithm. It will be appreciated by those of ordinary skill in the art that the natural exponential and logarithm can be replaced by the common exponential and logarithm to the base 10, respectively. Similarly, for the probe configuration in FIG. 2(c), the attenuation coefficient can be calculated as follows:

$$\alpha(\lambda) = \{1/\{z2'-z1'\}\} \ln\{I_{c1}(\lambda)^c / I_{c2}(\lambda)^c\} \quad (4)$$

Once the attenuation coefficient $\alpha(\lambda)$ is determined, the intrinsic fluorescence, $I_I(\lambda)$, can be restored from either of the signals $I_{c1}(\lambda)^c$ or $I_{c2}(\lambda)^c$ (preferably $I_{c2}(\lambda)^c$ where y2'<<y1') by assuming an average effective range "R" from which most of the intrinsic fluorescence is collected. For biological tissue, the constant "R" is approximately about 0.2 mm at 308 nm excitation radiation. Therefore, the intrinsic fluorescence $I_I(\lambda)$ can be obtained by substituting the measured $I_{c2}(\lambda)^c$ into equation (2) and solving for $I_I(\lambda)$ using the constant R and the known value y2':

$$I_I(\lambda) = I_{c2}(\lambda)^c e^{\alpha(\lambda) \cdot (R+y2')} \quad (5)$$

Whether the measured attenuation accounts for absorption and/or scattering is mainly determined by the wavelength band of interest and the nature of the sample. The optical properties of biological tissue and the effects of tissue on LIF are greatly different for the wavelengths below and above approximately 600 nm. Below about 600 nm, the optical attenuation of biological tissue is primarily due to absorption and, hence, the attenuation coefficient $\alpha(\lambda)$ will represent absorptivity $\alpha(\lambda)$. Absorptivity is a property of a substance, while absorbance is a property of a particular sample of a substance. Therefore, absorbance will vary with the concentration of the substance (e.g. hemoglobin) and geometry of the tip of the probe. Thus, for samples such as biological tissue where the attenuation of the sample is primarily due to absorption, the absorbance $A(\lambda)$ and the percent transmittance $\%T(\lambda)$ of the sample can be calculated as follows:

$$A(\lambda) = \log\{I_{c2}(\lambda)^c / I_{c1}(\lambda)^c\} \quad (6)$$

$$\%T(\lambda) = 100 \cdot \{I_{c1}(\lambda)^c / I_{c2}(\lambda)^c\} \quad (7)$$

Figure 3:
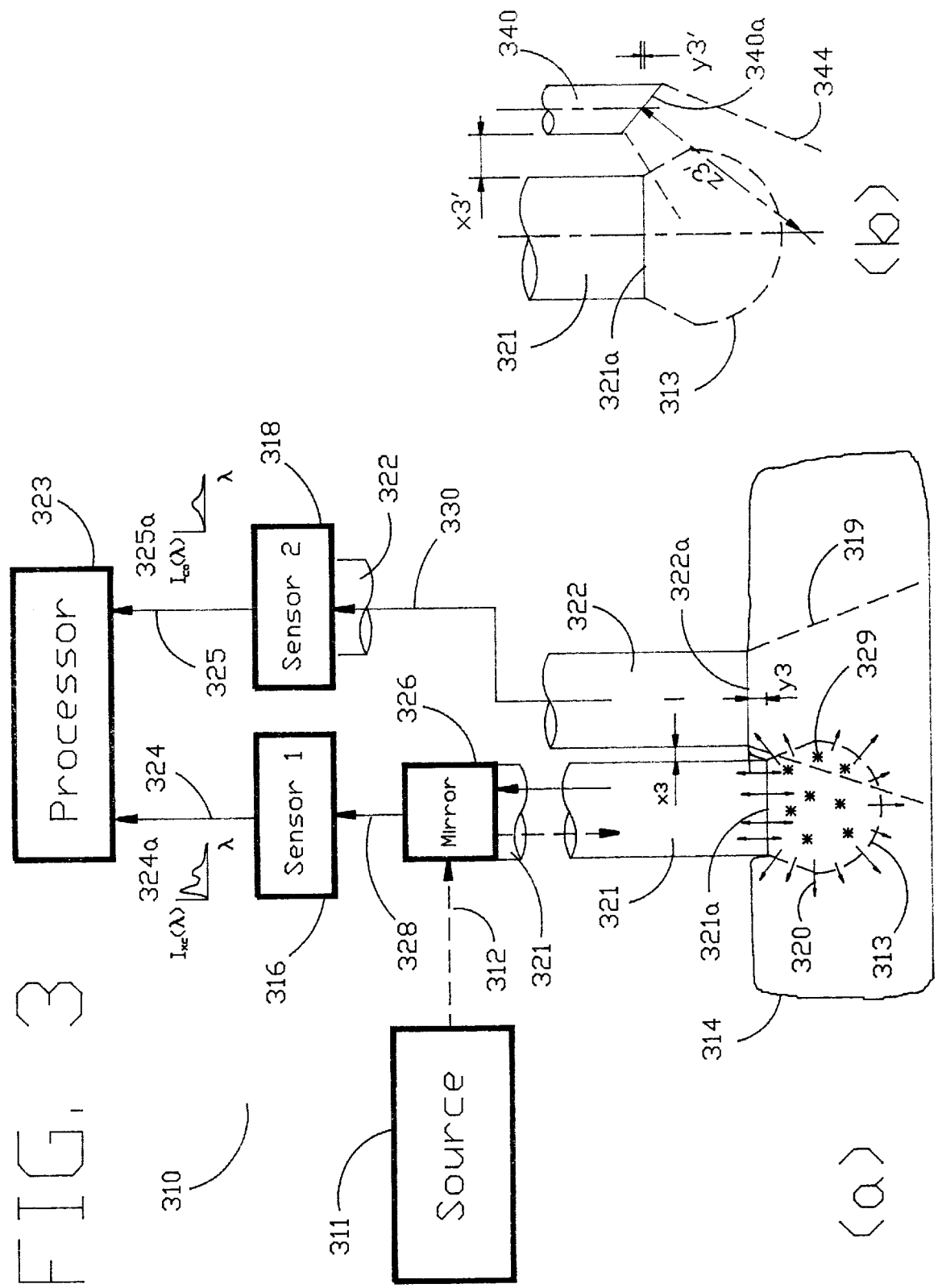
FIG. 3(a) is a schematic diagram of a LIFAS system in accordance with the present invention having a first excitation-collection waveguide and a second collection only waveguide.
FIG. 3(b) is a schematic diagram of an alternative configuration of the collection waveguides of FIG. 3(a)

In an alternative embodiment of the LIFAS system 310, shown in FIG. 3(a), the source 311 emits laser radiation 312 at a wavelength and intensity capable of inducing fluorescence of the sample 314. The laser radiation 312 is reflected by a dichroic mirror 326 into an excitation-collection waveguide 321, which transmits the laser radiation 312 to the sample volume 313 where the laser radiation 312 excites local fluorophores to emit intrinsic fluorescence 329. Furthermore, the intensity of the laser 312 should be sufficient to create a sample volume 313 that overlaps with the numerical aperture 319 of the collection-only waveguide 322. The dimensions of the sample volume 313 will also depend on the numerical aperture of the excitation-collection waveguide 321, on the wavelength and intensity of the excitation radiation 312 and on the optical properties of the sample 314. The intrinsic fluorescence 329 is modulated, for example, by the absorption and scattering of the local chromophores (not shown) and scatterers (not shown) of the sample 314.

The excitation-collection waveguide 321 collects a first portion 328 of the return light 320 directly from the sample volume 313. The first portion 328 of the return light 320 is transmitted through the dichroic mirror 326 to the first sensor 316. The first sensor 316 generates a first signal 324a representing the intensity $I_{xc}(\lambda)$ of the first portion 328 of the return light 320 at a plurality of wavelengths within a predetermined wavelength band.

As shown in FIG. 3(a), the collection-only waveguide 322 may be positioned such that the aperture 322a is laterally displaced from the excitation-collection waveguide 321 by the distance x3 and axially displaced from the aperture 321a of the excitation-collection waveguide 321 by the range y3. Preferably, the lateral distance x3 is zero while the axial distance y3 is non-zero. Also, the apertures 321a and 322a of the waveguides 321 and 322 are preferably positioned in close proximity to or in contact with the sample 314 during use of the LIFAS system 310, as shown in FIG. 3(a). Meanwhile, the numerical aperture 319 of the collection-only waveguide 322 is selected to include at least a portion of the sample volume 313.

The collection-only waveguide 322 collects a second portion 330 of the return light 320 which is transmitted to a second sensor 318. The second sensor 318 generates a second signal 325a representing the intensity $I_{co}(\lambda)$ of the second portion 330 of the return light 320 at a plurality of wavelengths preferably within the same wavelength bands as the signal 324a generated by the first sensor 316. Furthermore, a longpass filter is placed in front of the aperture of each of the sensors 316 and 318 to selectively block backscattered excitation radiation.

In the embodiment shown in FIG. 3(a), the first and second portions 328 and 330 of the return light 320 experience different attenuation effects due to the unequal pathlengths traversed by the return light 320 from the sample volume 313 to the apertures 321a and 322a of the waveguides 321 and 322, respectively. The second portion 330 of the return light 220 collected by the aperture 322a travels an additional path-length through the tissue as compared to the first portion 328 of the return light 320 which is collected by the aperture 321a directly from the sample volume 313. Hence, the first portion 328 of the return light 320 suffers less path-length-dependent attenuation as compared to the second portion 330 of the return light 320. Thus, the signals 324a and 325a representing intensity $I_{xc}(\lambda)$ and $I_{co}(\lambda)$ at different wavelengths will exhibit different levels of modulation caused by the sample 314.

The signals 324a and 325a will also exhibit wavelength-dependent modulations caused by the instrumental effects. The wavelength-dependent modulations due to instrumental effects can be determined and, in turn, compensated for by conducting a calibration of the LIFAS system 310. System calibration is performed using light from a standard lamp (Quartz Halogen Lamp, Model No. 63358, Oriel Instruments, Stratford, Conn.) having a predetermined continuous spectrum to measure the wavelength-dependent instrumental effects of the LIFAS system 310. Once these instrumental effects are known, the processor 323 can be adapted to correct the measured intensities $I_{xc}(\lambda)$ and $I_{co}(\lambda)$ for modulations caused by the wavelength-dependent instrumental effects. The corrected intensities $I_{xc}(\lambda)^c$ and $I_{co}(\lambda)^c$ representing the intensity of the first and second portions 328 and 330 of the return light 320 at different wavelengths can then be used by the processor 323 to determine the wavelength-dependent attenuation $\alpha(\lambda)$ of the sample 314. As discussed in detail, below, once the attenuation is known, either of the signals 324a or 325a, preferably 324a, can be corrected for the effects of attenuation to restore the intrinsic LIF 329 of the fluorophores in the sample volume 313.

In the preferred embodiment, the source 311 is an Xe—Cl excimer laser emitting ultraviolet excitation radiation at a wavelength of 308 nm. The waveguides 321 and 322 are advantageously comprised of optical fibers or optical fiber bundles, which can be integrated into a probe for ease of use and durability. A 1.4 mm diameter optical bundle and a 0.4 mm optical fiber are used as the excitation-collection and the collection-only waveguides, respectively. Preferably, the collection-only waveguide is a plurality of 0.4 mm optical fibers disposed about the periphery of the excitation-collection waveguide. The optical bundle and fibers are made of fused silica which is transparent to the 308 nm ultraviolet radiation. Furthermore, the probe may be configured within, for example, the shaft of a hypodermic needle, so that the in-vivo physiological or pathological properties of biological tissue can be determined. Each of the sensors 316 and 318 is a spectrograph (Model FF250, ARIES Inc., Concorde, Mass.) associated with a 1024 element intensified photo diode array (PDA) to image the resolved spectrum. Each PDA is connected to an optical multichannel analyzer (OMA III, EG&G Princeton Applied Research Corporation, Princeton, N.J.) which measures the intensity of the light spectrum imaged by the PDA and produce the signals 324a and 325a. The processor 323 is a personal computer that is networked to each of the sensors 316 and 318 via the signal paths 324 and 325 to receive the signals 324a and 325a, respectively.

The method of determining the attenuation coefficient $\alpha(\lambda)$ and the intrinsic fluorescence $I_T(\lambda)$ of a sample using the embodiment of FIG. 3(a) in accordance with the current invention is as follows. In the embodiment shown in FIG. 3(a), "D" represents the effective range, from which the collection waveguide 321 collects a majority of the portion 328 of the return light 320. The portion 328 of the return light 320 is collected directly from the sample volume 313 by the excitation-collection waveguide 321. Therefore, the wavelength-dependent intensity $I_{xc}(\lambda)^c$ of the portion 328 of the return light 320 collected by the excitation-collection waveguide 321 will be substantially similar to the wavelength-dependent intensity of the return light 320, represented as $I_o(\lambda)$. However, the return light 320 with the intensity $I_o(\lambda)$ will suffer additional wavelength-dependent attenuation as it travels the extra path-length to reach the aperture 322a and is collected as the second portion 330 of the return light 320 with the intensity $I_{co}(\lambda)^c$. The lateral and axial distances x3 and y3 will be predetermined by the configuration of the waveguides 321 and 322. In the preferred embodiment, the lateral distance x3=0 and the axial distance y3>0. Thus, the wavelength-dependent intensity $I_{co}(\lambda)^c$ can be approximated by the following equations:

$$I_{xc}(\lambda)^c \approx I_o(\lambda) = I_T(\lambda)e^{-\alpha(\lambda) \cdot D} \quad (8)$$

$$I_{co}(\lambda)^c \approx I_o(\lambda)e^{-\alpha(\lambda) \cdot y3} \quad (9)$$

$$\approx I_{xc}(\lambda)^c e^{-\alpha(\lambda) \cdot y3}$$

$$\alpha(\lambda) = \{1/y3\}\ln\{I_{cx}(\lambda)^c / I_{co}(\lambda)^c\} \quad (10)$$

Similarly, for the alternative probe configuration shown in FIG. 3(b), where the lateral distance x3'>0 and the axial distance y3'=0, the attenuation coefficient can be approximated as follows:

$$\alpha(\lambda)=\{1/x3'\}\ln\{I_{xc}(\lambda)^c/I_{co}(\lambda)^c\} \quad (11)$$

Once the attenuation coefficient $\alpha(\lambda)$ is determined, the intrinsic fluorescence, $I_T(\lambda)$, can be restored from either of the signals $I_{xc}(\lambda)^c$ or $I_{co}(\lambda)^c$, preferably $I_{xc}(\lambda)^c$, by assuming an average effective range "D" from which most of the intrinsic fluorescence is collected. For biological tissue, the constant "D" is approximately about 0.2 mm at 308 nm excitation radiation. By substituting the measured $I_{xc}(\lambda)^c$ into equation (7) and solving for $I_T(\lambda)$:

$$I_T(\lambda)=I_{xc}(\lambda)^c e^{\alpha(\lambda) \cdot D} \quad (12)$$

As discussed in connection with the previous embodiment, the measured attenuation may account for absorption and/or scattering depending on the wavelength band of interest and the nature of the sample. Below about 600 nm, the optical attenuation of biological tissue is primarily due to absorption and, hence, the attenuation coefficient $\alpha(\lambda)$ will represent absorptivity $\alpha(\lambda)$. Also, the absorbance $A(\lambda)$ and the percent transmittance $\%T(\lambda)$ of such samples can be calculated as follows:

$$A(\lambda)=\log\{I_{xc}(\lambda)^c/I_{co}(\lambda)^c\} \quad (13)$$

$$\%T(\lambda)=\{I_{co}(\lambda)^c/I_{xc}(\lambda)^c\}100 \quad (14)$$

Figure 4:
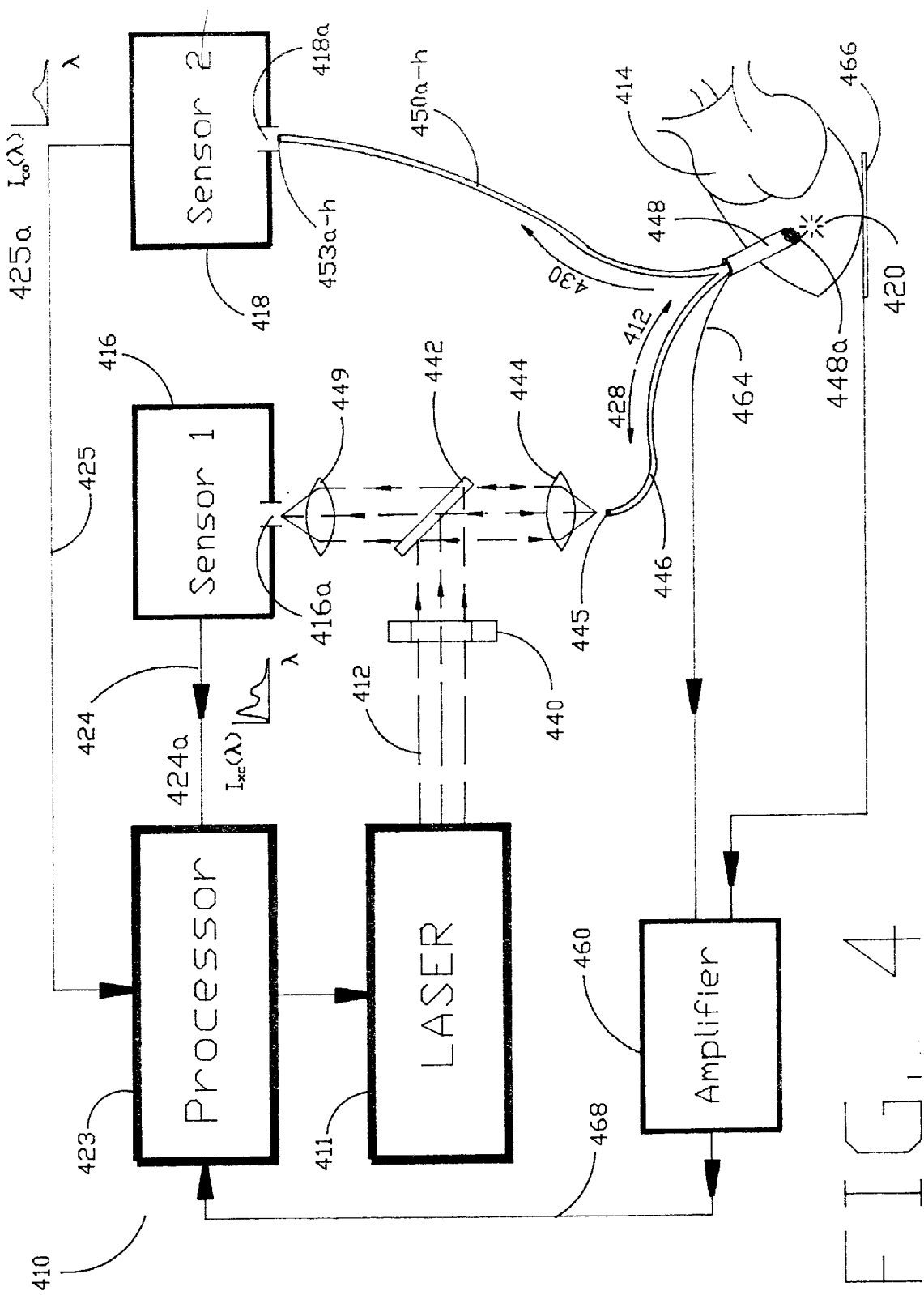
FIG. 4 is schematic diagram of a LIFAS system for biomedical applications in which excitation radiation is used to induce fluorescence of tissue.

In another alternative embodiment shown in FIG. 4, a LIFAS system 410 in accordance with the present invention has been adapted for biomedical applications. In this particular embodiment, the LIFAS system 410 has been adapted to determine the optical attenuation of biological tissue. The laser 411 emits radiation 412 at a wavelength capable of exciting the tissue 414 to emit fluorescence. The radiation 412 is directed through an iris 440 at a dichroic mirror 442 which reflects the radiation 412 onto a lens 444 which focuses the radiation 412 onto the proximal tip 445 of an optical fiber 446. The adjustable iris 440 is advantageously used to reduce the energy of the radiation 412. Alternatively, the adjustable iris 440 can be replaced by any suitable attenuator.

The probe 448 includes a central optical fiber 446 that is used as the excitation-collection fiber and peripheral optical fibers 450a–h are used as the collection-only fibers. The distal end of the optical fibers 446 and 450a–h are incorporated into the optical probe 448. The aperture 448a the optical fiber probe 448 is placed in proximity to the tissue 414 so that the aperture 446a of the excitation-collection fiber 446 and apertures 451a–h of the collection-only fibers 450a–h are in contact with the tissue 414. As shown in a partial perspective view in FIG. 5(a), the optical fiber probe 448 includes a central optical fiber 446 and a plurality of optical fibers 450a–h disposed about the periphery of the central optical fiber 446. The apertures 451a–h of the distal ends of the collection-only fibers 450a–h are axially displaced by a small distance y3 with respect to the aperture 446a of the excitation-collection fiber 446. The return light 420 collected by apertures 451a–h of the collection-only fibers 450a–h pool into the aperture 418a of the sensor 418. It will be appreciated by those in the art that the optical fibers 446 and 450a–h can advantageously be replaced by optical fiber bundles in order to obtain greater flexibility and durability. For example, as shown in FIG. 5(b), the central optical fiber 446 can be replaced with an optical fiber bundle 454.

The excitation radiation 412 is transmitted through the optical fiber 446 to the tissue 414 to induce intrinsic fluorescence of the fluorophores of the tissue 414. The intrinsic fluorescence is modulated, for example, by the chromophores and/or scatterers of the tissue 414. A first portion 428 of the return light 420 is collected by the optical fiber 446 from the tissue volume that is directly irradiated by the excitation radiation 412 and transmitted through the optical fiber 446 to a first lens 444 where the return light is directed through the dichroic mirror 442 and then focused by a second lens 449 onto the aperture 416a of a first sensor 416. Similarly, the collection-only optical fibers 450a–h collect a second portion 430 of the return light 420 and transmit the second portion 430 of the return light 420 to the second sensor 418. Preferably, longpass filters are placed in front of the apertures 416a and 418a of the sensors 416 and 418 to selectively block backscattered excitation radiation. A first signal 424a and a second signal 425a representing the intensity of the first and second portions 428 and 430, respectively, of the return light 420 are generated by the first and second sensors 416 and 418 and transmitted via signal paths 424 and 425 to the processor 423. The processor 423 uses the first and second signals 424a and 425a generated by the detectors 416 and 418 to determine the wavelength-dependent attenuation of the sample 414 using equations (8), (9) and (10) as described in the previous embodiment.

Figure 8:
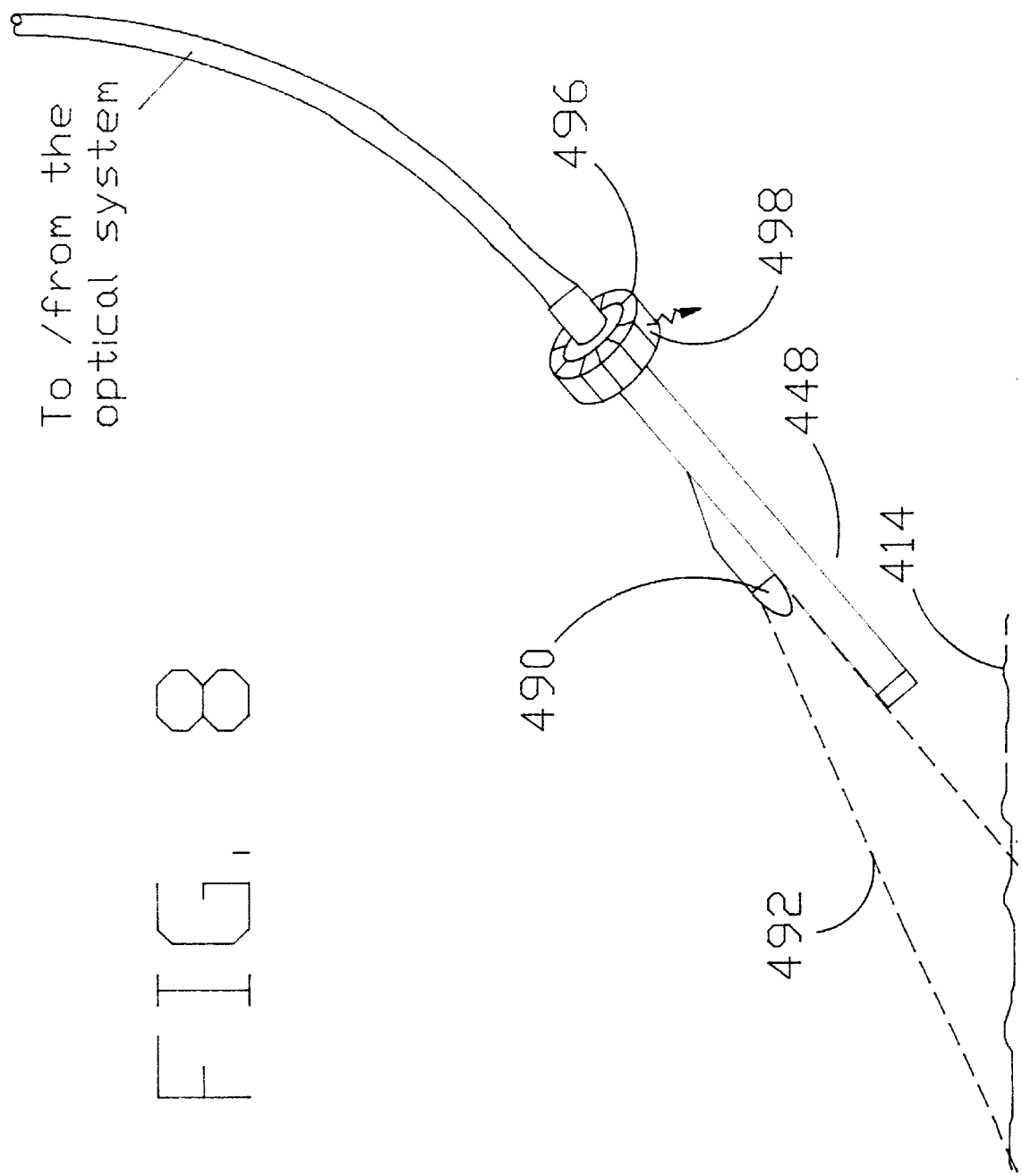
FIG. 8 is a perspective view of a probe incorporating a visible light source for probe positioning and a circular LED array for indicating the direction of contraction propagation.

In a particularly preferred embodiment of the LIFAS probe 448 shown in FIG. 8, an illumination source 490 emitting visible light 492 is mounted on the probe 448 to act as a spotlight for the operator. Because room illumination can contaminate the spectral measurements of the system 410 by adding background light, use of the illumination source 490 will allow the operator to see and accurately position the probe 448 under low-light conditions. The illumination source 490 is configured to illuminate the sample at all times, except when the LIFAS system is monitoring return light from the sample 414.

The biological electrical signal arising in nerves or contractile tissue, such as muscle, is known as the "action potential" and is caused by sudden changes in the ion conductivity of the cell membrane. The occurrence of an action potential in contractile tissue initiates a contraction. For example, in cardiac tissue, the action potential propagates and spreads in a wave-like manner to induce a local myocardial contraction wherever it travels.

An action potential propagating in the tissue local to the aperture 448a of the probe 448 can be detected by the electrode 464 which is incorporated into the probe 448 as shown, for example, in FIG. 6(a). Voltage alternations caused by the occurrence of the action potential are picked up by the electrode 464 in reference to the common electrode 466 and are transmitted to the amplifier 460. The common electrode 466 provides the electrical ground for the amplifier 460 by maintaining contact with the tissue of interest 414 or the whole body. As discussed in connection with FIG. 7, below, the amplified action potential 468 is transmitted to the processor 423 to trigger the acquisition process of the LIFAS system 410 at a pre-selected phase of the tissue contraction or of the cardiac cycle, whichever is applicable.

Figure 6:
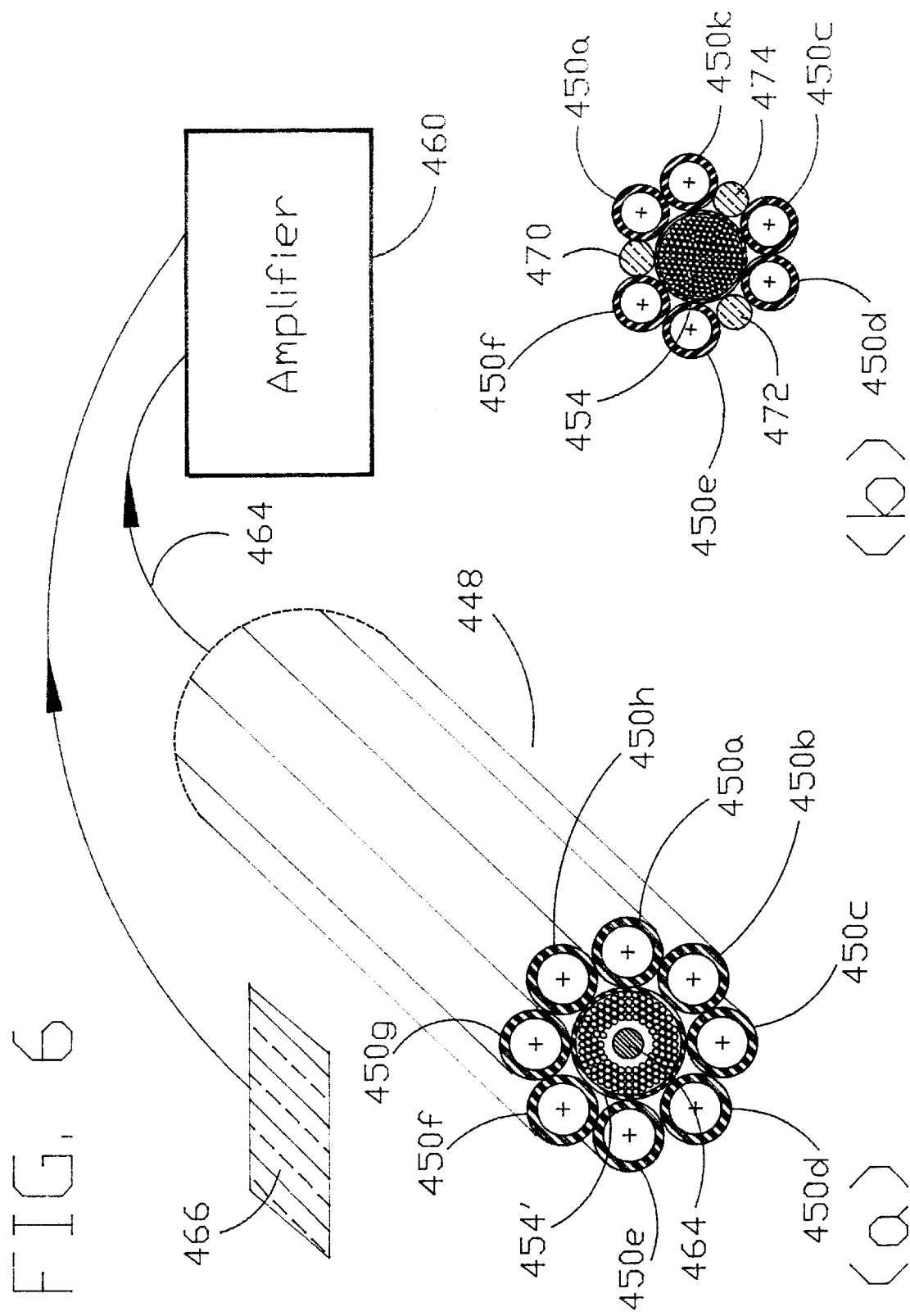
FIGS. 6(a) and (b) are partial perspective views of an electrical subsystem used to synchronize a LIFAS system with the electrical activity of tissue using electrodes integrated into the optical probe.
Figure 7:
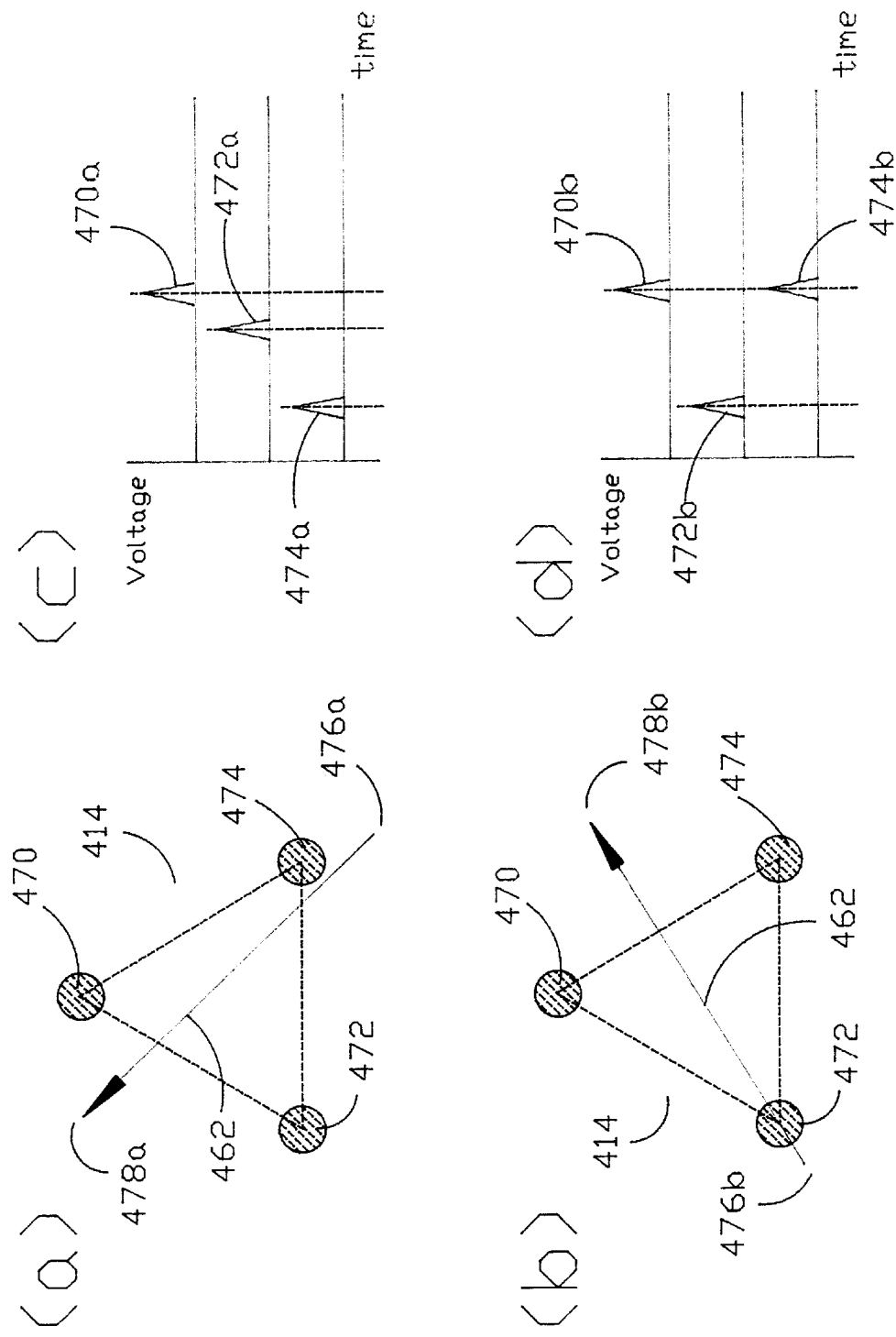
FIGS. 7(a) and (b) are schematic diagrams showing the relative positions of the action potential and electrodes integrated into the optical probe.
FIGS. 7(c) and (d) are the corresponding action potential timing diagrams.

In an alternative probe arrangement, a plurality of electrodes or fibers with a conductive coating can be distributed circumferentially about the tip of the optical fiber probe 448. For example, as shown in FIG. 6(*b*), the probe 448 can be equipped with three electrodes 470, 472 and 474 arranged in a triangular configuration. The action potentials measured by each of the electrodes 470, 472 and 474 are amplified through separate channels of the amplifier 460 and transmitted to the processor 423. As illustrated in FIG. 7, the processor 423 processes the received signals to determine the direction of propagation of the contraction vector 462. In particular, the processor detects the phase lead/lag between the action potentials collected by the electrodes 470, 472 and 474 to determine the orientation of the contraction vector 462 with respect to the location of the electrodes 470, 472 and 474.

For example, the contraction vector 462 shown in FIG. 7(*a*) is propagating from the tissue site 476*a* to the site 478*a* and, hence, as shown in FIG. 7(*c*), the action potential 474*a* arrives before the action potential 472*a* which in turn arrives before the action potential 470*a*. Moreover, the phase difference or time delay between a pair of action potentials indicates how the contraction vector 462 is centered between the location of the corresponding pair of electrodes. For example, as shown in FIG. 7(*b*), the contraction vector 462 propagates from the tissue site 476*b* to the site 478*b*. As a result, the corresponding time of arrival of action potentials 470*b*, 472*b* and 474*b*, as shown in FIG. 7(*d*), will vary. The processor 423 processes the signals and indicates the direction of the propagation of the contraction to the system operator. The direction of propagation can be indicated, for example, by a circular array 496 of light emitting diodes (LED) 498 mounted cirumferentially on the probe 448, as shown in FIG. 8. The processor 423 transmits a signal to the LED array 496 so that, for example, only the LED element pointing in the direction of contraction propagation would glow.

It will be appreciated that the amplifier 460 can be replaced by any device that can measure the electrical activity of biological tissue such as a differential amplifier, an electrocardiogram (ECG), an electromyogram (EMG), an electroencephalogram (EEG), depending on the LIFAS application. Furthermore, it will be appreciated that optical fibers with a metallic or electrically conductive coating can be used in place of one or all of the electrodes 464, 470, 472 or 474 to measure the action potential of the tissue. It should be noted that, conventional ECG is generally not suitable for triggering the acquisition of LIFS or LIFAS systems, since it does not accurately indicate the instantaneous state of myocardial contraction at the sample volume. However, customary ECG using limb or chest leads can be used to trigger data acquisition of the LIFAS system 410 where the sample 414 is non-contractile tissue.

In the LIFAS system 410 shown in FIG. 4, the light source 411 is preferably a lamp or a laser that emits ultraviolet, visible or infrared radiation. In the preferred embodiment, the source 411 is an XeCl excimer laser emitting pulses of ultraviolet excitation radiation at 308 nm. Where ultraviolet radiation is used, it is advisable that the optical components used in the acquisition system be made of synthetic quartz (fused silica) to ensure maximal ultraviolet transmission and minimal instrumental fluorescence. Alternatively, a nitrogen laser, a helium-cadmium laser, a frequency-multiplied laser, a solid-state laser, an arc lamp or a light-emitting diode can be used as the light source 411. The energy of the excitation light 412 is typically between 0.001–10 m Joules. However, it will be appreciated that the selected energy level should be low enough to avoid tissue ablation and/or photobleaching while still being adequate to produce detectable LIF.

In the preferred embodiment, the sensors 416 and 418 are each comprised of a spectrograph (Model FF250, ARIES Inc., Concorde, Mass.) associated with a 1024 element intensified photo diode array (PDA) detector. An optional low fluorescence, long-pass filter (not shown) with a cutoff wavelength above 308 nm, preferably 335 nm (Schott WG335), is placed before the entrance slit of each spectrograph to selectively block any backscattered excitation radiation from reaching the sensors 416 and 418. The entrance slit of the spectrograph preferably has a width of 100 micrometers. The spectrograph uses a 150 lines per millimeter diffraction grating to disperse the incoming return light 420 into its spectral components.

The spectrum formed by the spectrograph is imaged by a detector, preferably an intensified linear photodiode array (Model 1420, EG&G Princeton Applied Research Corporation, Princeton, N.J.) facing the output port of the spectrograph. The photodiode array generates a plurality of electrical signals representing the intensity of the return light 420 at wavelengths within predetermined wavelength bands. Alternatively, the sensors can be constructed of any suitable materials, such as individual light-sensitive diodes with appropriate band-pass filters for the analysis of spectral bands of the return light or an optical spectrum analyzer ("OSA") for analysis of a broader spectrum. Selection of the return light monitoring device will depend on a variety of factors, including cost, accuracy, resolution, and whether the user is interested in monitoring a single wavelength, a wavelength band or an entire spectrum.

Figure 5:
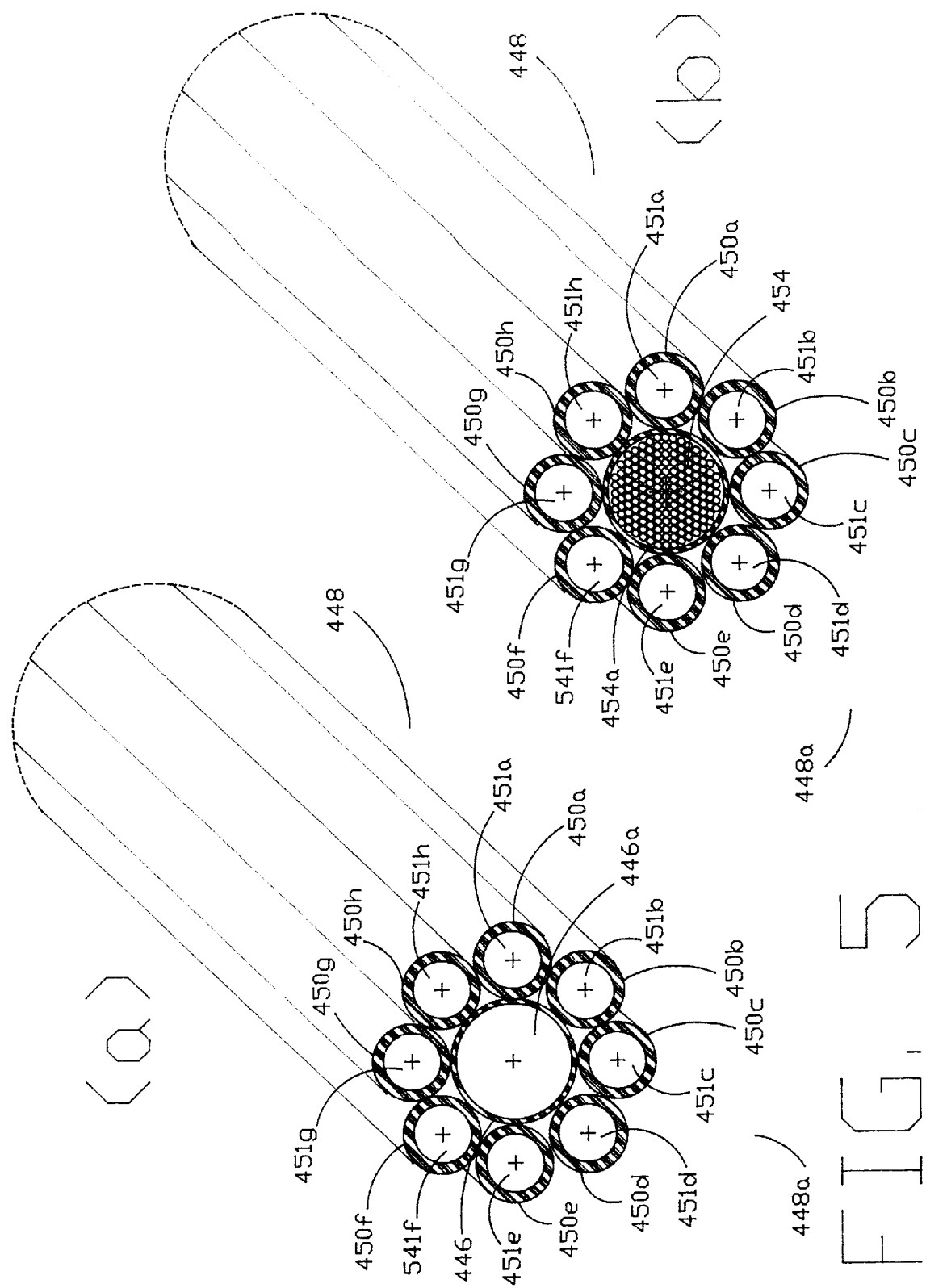
FIGS. 5(a) and (b) are end perspective views of a LIFAS probe having an optical fiber and an optical fiber bundle as the central waveguide.

Although in the preferred embodiments shown in FIGS. 4 and 5, the optical fiber probe includes a central excitation-collection optical fiber or optical fiber bundle with a plurality of collection-only optical fibers disposed around its periphery, it will be appreciated by those of ordinary skill in the art that the probe can take many forms. Furthermore, it will be appreciated that the central optical fiber can be used as the collection-only waveguide while all or some of the peripheral fibers can be used for excitation-collection or collection-only. The latter arrangement is preferred when testing highly-attenuating samples to achieve a better signal-to-noise ratio.

Figure 9:
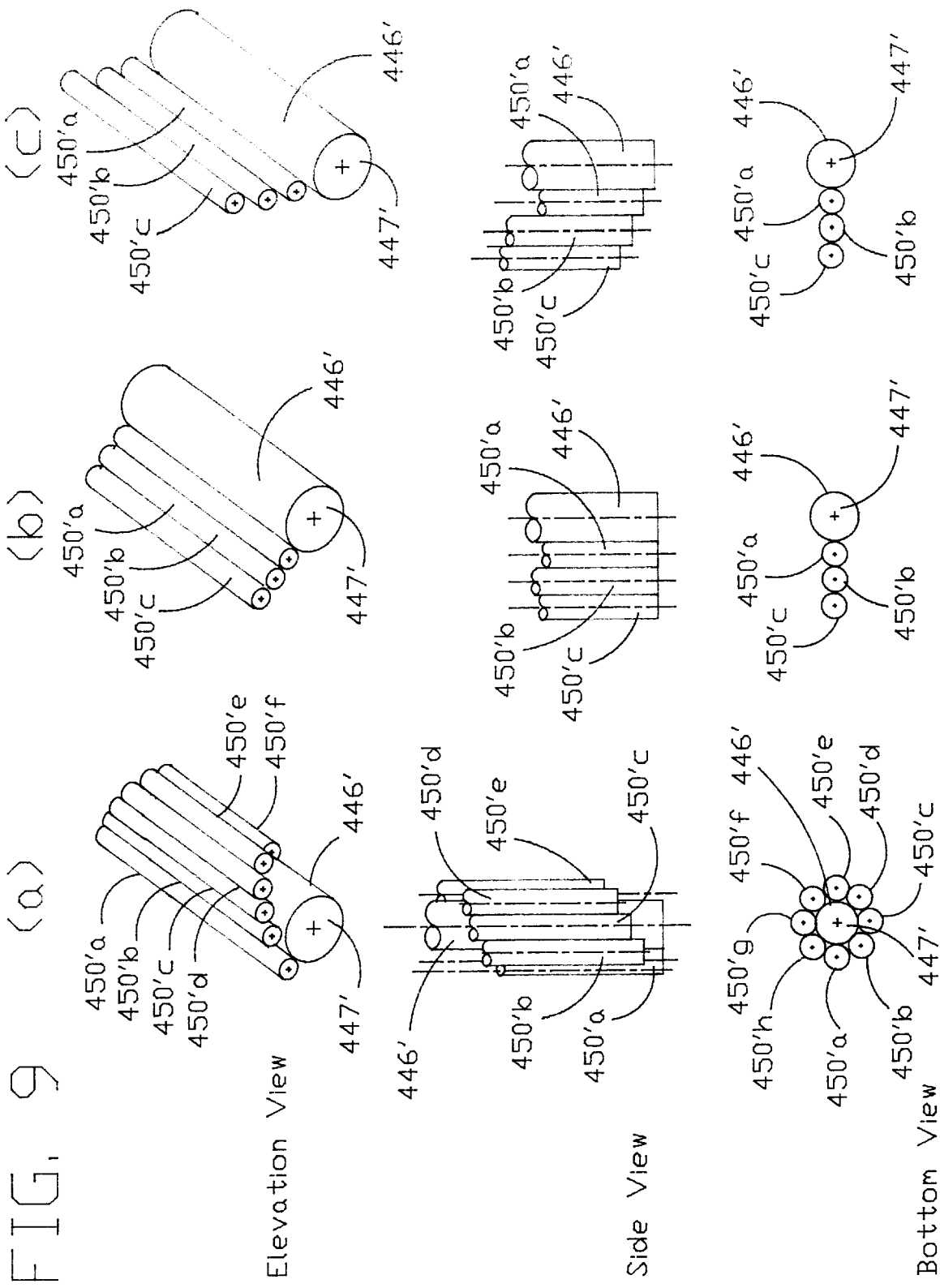
FIGS. 9(a)–(c) are partial perspective views of three LIFAS probes having waveguides arranged in different geometrical configurations adapted for different applications.

FIG. 9 shows three alternative geometrical configurations of the collection-only optical fibers 950*a–h* about the excitation-collection waveguide 946. In these embodiments, it is desirable to couple each of the collection-only waveguides 950*a–h* to a separate sensor so that the intensity of each portion of the return light collected by each fiber can be monitored. In FIG. 9(*a*), the collection-only waveguides 950*a–h* are arranged about the excitation-collection waveguide 946 so that their apertures have a helical configuration. Because the aperture of each successive collection-only waveguide is shifted axially away from the aperture 947 of the excitation-collection waveguide 946, the return light collected by each of the collection-only waveguides 950*a–h* will be attenuated in varying degrees. Use of a probe arrangement having a plurality of collection distances will be useful in measuring the polarization and/or the attenuation of especially, a sample having a higher sensitivity to attenuation due to absorption. Furthermore, a probe incorporating a plurality of collection distances have application to a larger variety of samples. For example, where the sample is highly attenuating, the collection-only waveguides having apertures close to the excitation site can be used to collect the return light. Where the sample is lightly attenuating, the return light collected by the waveguides having apertures that are further from the excitation site will be useful in determining the attenuation.

In FIG. 9(b), the collection-only waveguides 950a–c are displaced laterally with respect to the excitation-collection waveguide 946. Such a probe configuration will be useful in measuring the polarization and/or the attenuation of the sample where the sample has a higher sensitivity to attenuation due to scattering. The return light collected by the waveguide 950c will be useful in measuring attenuation of a lightly attenuating sample. On the other hand, the return light measured by the closest waveguide 950a will be useful in measuring the attenuation of a heavily-attenuating sample.

In FIG. 9(c), the collection-only waveguides 950a–c are both axially and laterally displaced with respect to the excitation-collection waveguide 946. This configuration combines the advantages of both of the aforementioned configurations shown in FIGS. 9(a) and 9(b).

Figure 10:
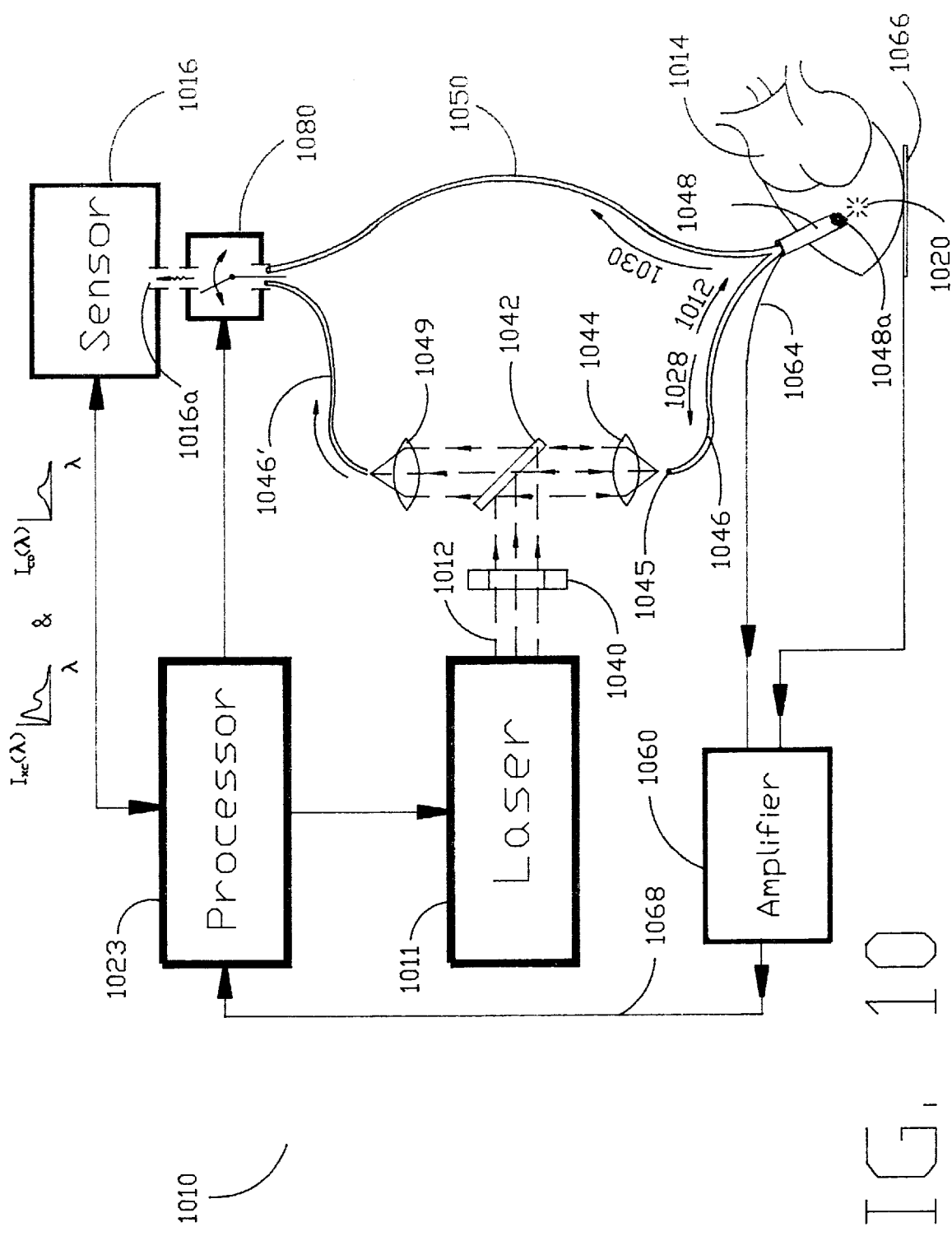
FIG. 10 is a schematic diagram of a biomedical LIFAS system in accordance with the invention in which a single optical detector is used to measure the return light from two collection fibers.

In an alternative embodiment of the LIFAS system of FIG. 4, shown in FIG. 10, a single sensor 1016 and an associated optical multiplexer 1080 are utilized. The multiplexer 1080 is used to switch the input of the sensor 1016 between the excitation-collection optical path (1046, 1044, 1042, 1049, 1046') and the collection-only optical path (1050) such that the return light from each pathway is measured sequentially. The processor 1023 sends trigger signals to the source 1011, the sensor 1016 and the optical multiplexer 1080 to synchronize their actions. If the source 1011 is a pulsed laser, two or more radiation pulses are typically required to acquire a single attenuation measurement using the multiplexed system 1010. A single laser pulse can be used if the laser pulse lasts long enough to sustain the emission of return light 1020 during the minimum period of time required by the optical multiplexer 1080 and associated sensor 1016 to acquire the spectral measurements from both the excitation-collection and the collection only optical paths. The preferred embodiment of the LIFAS system 1010 is similar to that of 410, except that the system 1010 utilizes an electromagnetic dual port shutter as the optical multiplexer 1080 associated with a single sensor 1016 in a configuration where the portion 1028 and the portion 1030 of the return light 1020 are measured sequentially.

Diagnosis of Hypoxia and Ischemia

The LIFAS methods and devices of the present invention can be used advantageously for the in-vivo diagnosis of hypoxia and ischemia of biological tissue. Hypoxia is a deficiency in the amount of oxygen reaching the tissue, e.g., due to pneumonia, whereas, ischemia is a localized reduction in arterial blood perfusion, e.g., due to a narrowing of arteries by spasm or disease. Ischemia can also result from hemorrhage of an arterial wound or during surgical procedure that temporarily interrupts the blood flow to a body region. The present invention describes new criteria and methods for the discrimination between normal, ischemic and hypoxic biological tissue, including, in particular renal and myocardial tissue, as follows.

Utilizing LIFAS methods and devices, it has been found that ischemic (or hypoxic) tissue exhibits a lower laser induced fluorescence attenuation ("LIFA") than normal tissue of the same type. Since LIFA is an absolute quantity, its magnitude can be directly compared with predetermined standard values. Similarly, in absorption-dominant media, the absorbance or percent transmittance can also be utilized. It has been found that, although the LIFA of ischemic tissue is lower than the LIFA of normal tissue over all wavelengths, their difference is most prominent between 350 and 450 nm.

The LIFAS-derived LIFA spectra of normal and ischemic rabbit kidney are shown in FIG. 12. The LIFA spectra shown in FIG. 12 are acquired using a LIFAS system employing 308 nm excitation radiation produced by an XeCl excimer laser. This LIFAS system uses a 335 nm longpass filter (Schott WG335) to cutoff backscattered excitation radiation form the collected return light. Hence, for this particular LIFAS system the LIFA values below 350 nm are not reliable. For biological tissue, the LIFA values in the wavelength band about 480 nm have the highest signal-to-noise ratio and hence measurement accuracy. As shown in FIG. 12, the LIFA of ischemic tissue is lower than the LIFA of normal tissue over the entire spectrum and is particularly low in the region from 350 to 450 nm.

As demonstrated in FIG. 12, the LIFA, absorbance or percent transmittance at a predetermined wavelength or wavelength bands can be used for the detection of ischemia or hypoxia. Furthermore, predictive models, spectral recognition techniques and associated classifiers can be applied to identify whether a given LIFA, absorbance or percent transmittance spectrum has been acquired from normal, ischemic or hypoxic tissue. The classifiers can be initially trained with LIFA, at a predetermined wavelength or wavelength bands acquired from tissue with a known state of perfusion or oxygenation.

Figure 13:
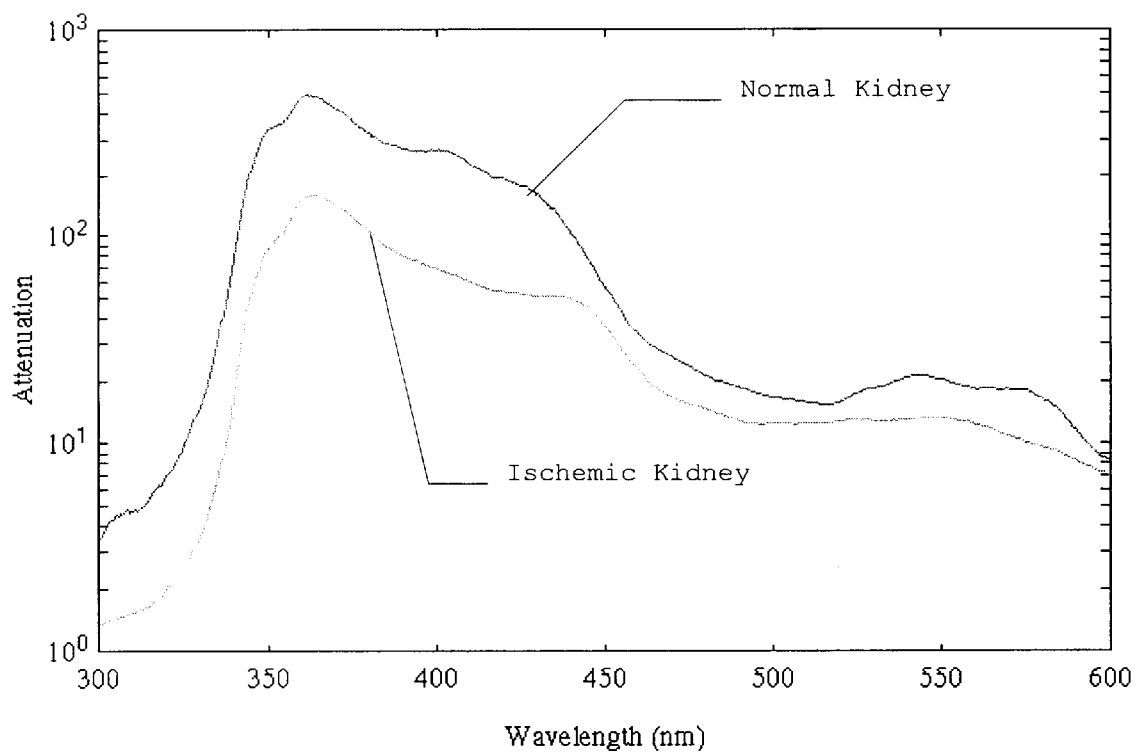
FIG. 13 is a scatter plot of the fluorescence intensity at 480 nm acquired from hypoxic (+), normal (o) and hyperoxic (x) tissue through excitation-collection and collection-only waveguides.

Another parameter found to be useful in the classification of normal, ischemic and hypoxic tissue, is the intensity of return light from a pair of LIFAS collection pathways (i.e. $[I_{c_1}(\lambda)^c, I_{c_2}(\lambda)^c]$ or $[I_{xc}(\lambda)^c, I_{co}(\lambda)^c]$ for the LIFAS embodiments described above.) For example, FIG. 13 shows the $[I_{xc}(\lambda)^c, I_{co}(\lambda)^c]$ pair at $\lambda$=480 nm, symbolized as $[I_{xc}(480)^c, I_{co}(480)^c]$, measured from hyper-oxygenated (x), normal (o) and oxygen deficient (+) rabbit kidney. The $[I_{xc}(480)^c, I_{co}(480)^c]$ from normal and oxygen deficient tissue tend to cluster in two linearly separable regions of the two dimensional $I_{xc}(\lambda)^c$–$I_{co}(\lambda)^c$ space. Thus, a simple linear or non-linear classifier function can be trained on a set of $[I_{xc}(\lambda)c, I_{co}(\lambda)^c]$ pairs measured using a LIFAS system from normal, ischemic and hypoxic tissue. Other classifiers such as artificial neural networks (ANN) are also being used. The trained classifier function can then be used to classify an unknown $[I_{xc}(\lambda)^c, I_{co}(\lambda)^c]$ pair as normal, ischemic or hypoxic. A "nearest neighbor" (NN) classifier has been found to perform satisfactorily. The NN classifier checks the proximity of an unknown $[I_{xc}(480)^c, I_{co}(480)^c]$ pair to clusters of predetermined $[I_{xc}(480)^c, I_{co}(480)^c]$ pairs measured from known normal, ischemic and hypoxic tissue. Other classifiers such as artificial neural networks (ANN) can also be utilized. For myocardial and renal tissue it has been found that it is preferable to use $[I_{xc}(\lambda)^c, I_{co}(\lambda^c)]$ measured at 480 nm, to optimize signal-to-noise ratio. However, $[I_{xc}(\lambda)^c, I_{co}(\lambda)^c]$ at other single or multiple pre-selected wavelengths can also be used.

An additional parameter for the classification of normal, ischemic and hypoxic tissue, is the wavelength of the peak transmittance of the tissue, symbolized hereafter as $\lambda_{max-T}$, especially in the 450–500 nm band. An alternative to $\lambda_{max-T}$ is the wavelength of the peak $I_{co}(\lambda)^c$ in the 450–500 nm band, symbolized hereafter as $\lambda_{max-co}$. Both $\lambda_{max-T}$ and $\lambda_{max-co}$ shift towards shorter wavelengths as the hemoglobin in the tissue becomes deoxygenated. For example, FIG. 14 shows $I_{co}(\lambda)^c$ spectra that are acquired using the LIFAS system shown in FIG. 10 employing 308 nm excitation radiation produced by and XeCl excimer laser. It should be noted that the $\lambda_{max\text{-}co}$ of normal tissue shifts to a shorter wavelength as the tissue becomes hypoxic; whereas the $\lambda_{max\text{-}co}$ of normal tissue shifts to a longer wavelength as the tissue becomes hyperoxic. Specifically, $\lambda_{max\text{-}co}$ varies between about 480 and 500 nm as blood or hemoglobin oxygenation varies between deoxygenated to oxygenated, respectively. A separation border can be identified at about 489.5 nm to separate $\lambda_{max\text{-}co}$ of normal tissue (peaks above 489.5 nm) from hypoxic/ischemic tissue (peaks below 489.5 nm). A simple classifier can be trained to identify tissue as hypoxic if its $\lambda_{max\text{-}co}$ is below 489.5, and vice versa. The degree of hypoxia is determined from the magnitude of the shift in $\lambda_{max\text{-}co}$ from the normal value, the smaller the shift the subtle the hypoxia.

The presence of renal or myocardial ischemia can be detected from the shape of the main lobe of the common LIF (e.g. $I_{xc}(\lambda)^c$) spectrum in the wavelength band 350–450 nm. The common LIF can be acquired via an excitation-collection waveguide of a LIFAS or a conventional LIFS system. For example, FIGS. 16(a) and (b) show typical LIF spectra acquired from normal and ischemic rabbit kidneys at an excitation wavelength of 308 nm. As shown in FIG. 16(b), the shape of the main lobe of the LIF acquired from normal tissue is skewed to the right (a positive skewness value). However, the shape of the main lobe of the LIF acquired from ischemic tissue is almost symmetric (a very small skewness value).

Figure 16:
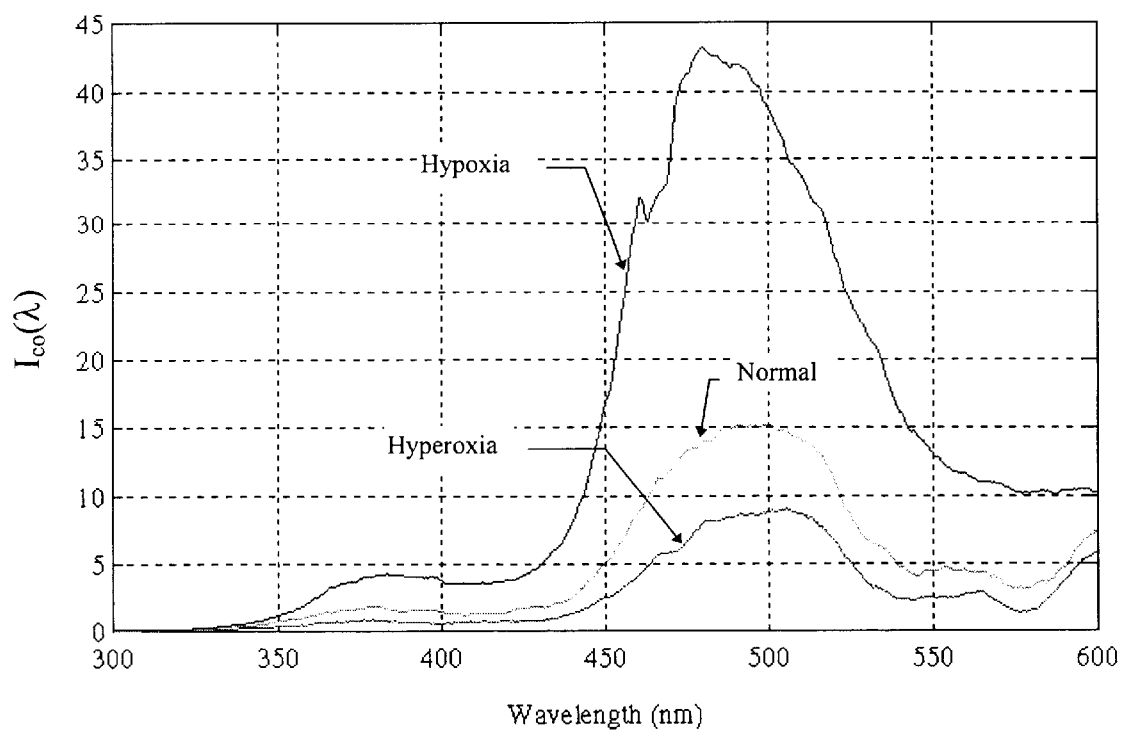
FIGS. 16(a) and (b) are graphs of typical modulated LIF spectra of normal and ischemic kidney, respectively, depicting the difference in the symmetry of the main lobe.

Skewness can be measured by a single parameter which indicates the degree of asymmetry of a lobe or curve around its mean value. For a symmetrical lobe the skewness is zero, however for an asymmetrical lobe the skewness can be either positive or negative depending on the shape. The skewness "S" is given by:

$$S = \frac{1}{N}\sum_{\lambda=1}^{N}(X_\lambda - \bar{x})^3 \quad (15)$$

$$\bar{x} = \frac{1}{n}\sum_{\lambda=1}^{N}X_\lambda \quad (16)$$

where x is the intensity of the fluorescence at the wavelength $\lambda$, $\bar{x}$ is the mean intensity of the lobe, $\lambda$ is the wavelength and N is the number of wavelength measurements in the lobe. Therefore, tissue ischemia can be detected by monitoring the skewness of the main lobe of a common (i.e. modulated) LIF acquired using an excitation-collection fiber from the tissue. A zero or negative skewness value indicates that the LIF spectra is acquired from ischemic tissue, while a positive skewness will indicate normally perfused tissue. The bottom of the central spectral valley is considered as the baseline for the definition of the main lobe as indicated in FIG. 16.

Figure 15:
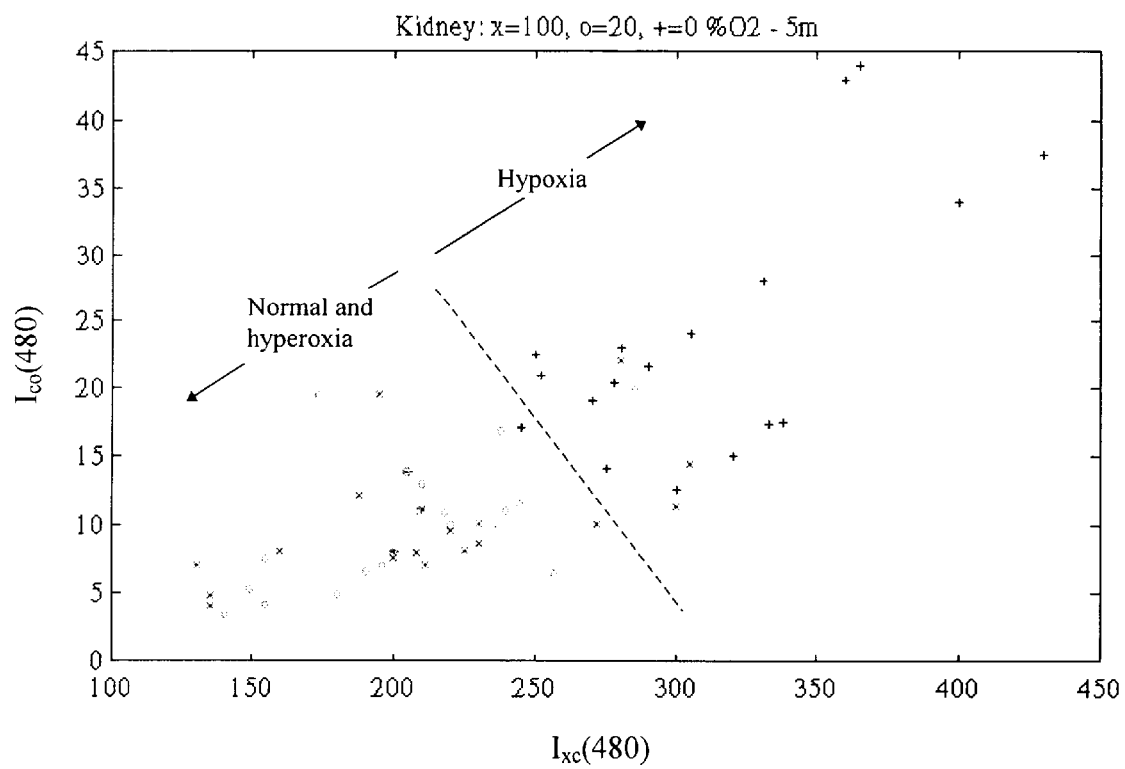
FIG. 15(a) is a graph of the modulated LIF spectra of normal and ischemic kidney.
FIG. 15(b) is a graph of the intrinsic LIF spectra of normal and ischemic kidney.

The intrinsic LIF of normal biological tissue will have a spectrum with a single peak resembling that of the main tissue fluorophores, collagen and elastin. However, in the event of ischemia or hypoxia the intrinsic LIF develops a secondary peak or a hump at about 470–490 nm which is associated with the peak fluorescence emission of NADH. The appearance of this hump in an intrinsic LIF spectrum is a direct indication of oxygen deficiency resulting from hypoxia or ischemia. Unfortunately, this NADH-related hump is not readily detectable in common LIF spectra because of an overlapping spurious hump created by an intensity dip associated with peak hemoglobin absorption at about 410 nm. For example, in common and intrinsic LIF spectrum of normal and ischemic rabbit myocardium shown in FIGS. 15(a) and (b), respectively, the intrinsic LIF spectrum of normal kidney does not exhibit the second hump created by the spectral valley associated with hemoglobin absorption. To the contrary, the intrinsic fluorescence of hypoxic myocardium exhibits a secondary hump indicating high NADH concentration. Accordingly, ischemia or hypoxia can be detected from a LIFAS-derived intrinsic LIF spectrum by assessing its NADH-related secondary hump either visually or through simple qualitative analysis. The magnitude of the NADH hump will indicate the level of oxygen deficiency caused by hypoxia or ischemia while its absence indicate normal oxygenation.

Classification using Chemometric Models

Current ischemia or hypoxia detection techniques use predetermined ratios of spectral intensities at wavelengths associated with NADH, elastin and collagen to discriminate normal from abnormal tissue. However, the magnitude of the intensity does not fully characterize spectral changes associated with ischemia or hypoxia. Instead, it is desirable to undertake spectral classification based on the shape of wavelength bands or the whole spectrum.

The introduction of the LIFAS methods and devices of the present invention enables the application of a new modeling approach for the measurement of ischemia and hypoxia. The approach relies on methods of multivariate linear regression (MLR), principle component regression (PCR) and the method of partial least squares (PLS). These modeling methods are well-established chemometric techniques used in the field of analytical chemistry to estimate the concentration of a material in a mixture from absorption spectra of the mixture. The algorithms and theoretical basis for PLS predictive modeling can be found in Brereton, R. G. *Chemometrics: Applications of Mathematics and Statistics to Laboratory Systems*, New York: Ellis Horwood, 1990. A basic overview of the PLS regression can be found in Gerald and Kowalski, "Partial Least-Squares Regression: A Tutorial" *Analytical Chimica Acta* 185 (1986): 1–17.

In the preferred embodiment, the MLR, PCR and the PLS models are trained with LIFA or absorbance spectra as their input and the concentration of both oxygenated and deoxygenated hemoglobin as their outputs. The blood content (i.e. quantity of blood) in the tissue is determined by combining the concentrations of both oxygenated and deoxygenated hemoglobin. The MLR, PCR and the PLS models are trained with LIFA spectra from normal, hypoxic or ischemic rabbit heart and kidney.

Once a model is trained, it can be used to predict the concentrations of oxygenated and deoxygenated hemoglobin if given a LIFA spectrum measured from tissue with unknown oxygenation. The presence and level of hypoxia can be determined by comparing the latter-predicted concentrations values to those known values previously measured from normal tissue. Hypoxic tissue has less oxygenated and more deoxygenated hemoglobin concentrations than normal tissue. Similarly, the presence and level of ischemia can be determined by combining the predicted concentrations to determine the total blood content and then comparing the total blood content to known values of blood content measured in normal tissue. Ischemic tissue will have a lower blood content than normally perfused tissue. The PLS model was found to have the optimal accuracy in detecting the presence and level of ischemia and hypoxia.

Although LIFA or absorbance spectra are the optimal input to the MLR, PCR or PLS models for concentration prediction, it will be appreciated that modulated LIF, or percent transmittance spectra can also be used due to the fact that, even though common LIF represent fluorescence information, the LIF spectra are modulated by wavelength-dependent tissue attenuation.

The MAM Classifier

In accordance with the invention, a new mathematical classifier has been developed and applied to categorize spectral data for ischemia or hypoxia detection. The recent multicriteria associative memories (MAM) technique is modified to perform as a data classifier. Similar to existing classifiers, the MAM requires initial training on a set of input-output data pairs. The training process of the MAM classifier involves the calculation of the weights matrix $M(\eta)$ from the input-output data set using the following learning rule:

$$M(\eta) = \eta RS^T[\eta SS^T + (1-\eta)I]^{-1} \quad (17)$$

The matrices "S" and "R" holds the input and output training vectors as their columns, respectively. The superscripts $^T$ and $^{-1}$ indicate matrix transpose and inversion, respectively, and "I" is the identity matrix. The parameter $\eta$ is initially set to 0.98; however, it can assume any value between 0 and 1 depending on the noise of the system. Following the training stage, the output "r" for an unknown input "s" can be readily calculated from the dot product:

$$r = M(\eta) \cdot s \quad (18)$$

Finally, an appropriate transfer function is used to assign the output "r" into one of several predetermined classification categories.

In the present invention, the MAM classifier is initially trained with LIFA (or absorbance) spectra acquired from normal or ischemic tissue as the training inputs. The corresponding normal or ischemic state can be encoded as, for example, "−1" or "1," respectively and used as the training outputs. Therefore, the training LIFA spectra are placed as columns of the input matrix "S" while their corresponding state-coded values are arranged in the same order as elements of the output row vector "R." The number of columns in "S" and elements in "R" are equal to the number of available training sets. A trained MAM matrix can determine whether an unknown LIFA spectrum "$s_?$" has been acquired from normal or ischemic tissue by calculating the dot product $r_? = M(\eta) \cdot s_?$ and passing the scalar result "$r_?$" to a hard limit transfer function. The hard limit transfer function then converts any negative or positive values of "$r_?$" into "0" or "1" indicating a normal or ischemic classification, respectively.

In a similar fashion, the MAM classifier can be applied for the detection of hypoxia and the discrimination between normal, ischemic and hypoxic tissue. It should be apparent that common or intrinsic LIF spectra can replace LIFA spectra as the classifier input. In addition, this input can be an entire spectrum, a re-sampled version of a spectrum or a set of statistical parameters or features characterizing a spectrum. Similarly, actual ischemia or hypoxia levels can be used as the classifier outputs instead of the binary coded output values employed in the above demonstration. In this case a linear transfer function may be used to categorize the output "r" of the MAM classifier.

The MAM technique outperformed the commonly-used artificial neural network (ANN) classifier in accurately classifying LIF/LIFA spectra resulting from normal and ischemic tissue. The superiority of the MAM classifier is most probably due to its insensitivity to spectral noise that might be present in LIF/LIFA spectra measured from biological systems. Although the foregoing MAM classifier is currently applied to discriminate spectral data for the purpose of ischemia or hypoxia detection, it is understood that those skilled in the art may apply it in various ways for different classification purposes.

Tissue Characterization

It will also be appreciated that the LIFAS devices and methods can be applied to tissue characterization, i.e., to differentiate between normal and diseased tissue, for tissue diagnostics and malignancy detection. Current LIFS techniques use the intensity spectrum of modulated LIF to identify malignant (cancerous and pre-cancerous) tissue and classify its type. LIFAS techniques offer a unique tissue characterizing capability not offered by conventional LIFS, based upon measurement of the attenuation spectrum.

A simple demonstration of LIFAS diagnostic capability is shown in FIGS. 17(a)–(d). Although normal kidney and heart tissue are different in nature, their common LIF spectra, shown in FIGS. 17(a) and (b) are almost identical and, hence, are not so useful for classification purposes. However, heart and kidney LIFA spectra, shown in FIGS. 17(c) and d are different in terms of both shape and peak attenuation values. Thus, LIFAS techniques offer better tissue identification power than conventional LIFS techniques.

Other biomedical applications of the LIFAS methods and devices will include laser removal of decorative tattoos, detection of the in-vivo glucose level, assessment of the degree of burn trauma, detection of atherosclerotic plaque, angioplasty, measurement of acidity or alkalinity, pH measurement, the analysis of biochemical fluids, and the like. For example, measurement of the in vivo skin absorption using LIFAS methods and devices in accordance with the present invention can aid in the selection of optimal laser wavelengths for removing tattoos of different colors. Furthermore, since LIFAS techniques can be used to determine absorbance from a hypodermic sample volume, the skin color and the depth of the tattoo dye can be more accurately characterized than in surface reflectance techniques. Similarly, burn injury assessment can be accomplished by using LIFAS techniques to measure the depth of burn by probing for the presence of blood perfusion at varying locations within the tissue. LIFAS techniques can also be used to determine the absorbance or turbidity of a liquid in-situ without the necessity of extracting a sample for use in a spectrometer.

It will be understood by those of ordinary skill in the art that, although the LIFAS system and method is shown in the exemplary method as applied to biological tissue, it is also readily applicable to chemical and industrial material. For example, LIFAS devices and methods can be used to measure the absorbance and/or turbidity of materials and mixtures in medical, food, beverage, detergent, plastic, glass, oil, paint, textile, and semiconductor applications. Furthermore, the concentration of the pure components of the mixture can be determined from the absorbance spectrum using chemometric techniques such as multivariate regression (MLR), partial least squares (PLS) or artificial neural networks described above.

Although the foregoing discloses preferred embodiments of the present invention, it is understood that those skilled in the art may make various changes to the preferred embodiments without departing from the scope of the invention. The invention is defined only by the following claims.

We claim:

1. A spectroscopic method of analyzing a sample, comprising:

irradiating a sample with radiation to produce fluorescence from the sample, wherein the fluorescence is modulated by the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence to determine a modulation characteristic of the sample.

2. The method of claim 1, wherein the radiation comprises substantially monochromatic light.

3. The method of claim 1, wherein the radiation comprises laser light.

4. The method of claim 1, wherein irradiating the sample comprises directing radiation at the sample using a waveguide.

5. The method of claim 4, wherein the waveguide is an optical fiber.

6. The method of claim 4, wherein the waveguide is an optical fiber bundle.

7. The method of claim 1, wherein monitoring of the modulated fluorescence comprises:

collecting a portion of the modulated fluorescence; and determining the intensity of the collected portion of modulated fluorescence.

8. The method of claim 7, wherein the first portion of the modulated fluorescence is collected with a first waveguide and the second portion of the modulated fluorescence is collected with a second waveguide.

9. The method of claim 8, wherein the first waveguide is an optical fiber.

10. The method of claim 8, wherein the first waveguide is an optical fiber bundle.

11. The method of claim 8, wherein the second waveguide is an optical fiber.

12. The method of claim 8, wherein the second waveguide is an optical fiber bundle.

13. The method of claim 1, wherein irradiating the sample comprises directing radiation to the sample using a first waveguide and wherein the fluorescence is monitored using the first waveguide.

14. The method of claim 7, wherein the intensity of the collected portion of the fluorescence is determined with a sensor.

15. The method of claim 7, wherein the intensity of the first portion of the modulated fluorescence is determined with a sensor.

16. The method of claim 7, wherein the intensity of the second portion of the modulated fluorescence is determined with a sensor.

17. The method of claim 7, wherein the intensity of the first portion of the modulated fluorescence is determined with a first sensor and the intensity of the second portion of the modulated fluorescence is determined with a second sensor.

18. The method of claim 7, wherein the first and second portions of the modulated fluorescence are measured consecutively.

19. The method of claim 7, wherein the first and second portions of the modulated fluorescence are measured simultaneously.

20. The method of claim 11, wherein the method further includes determining the intrinsic fluorescence of the sample.

21. The method of claim 1, wherein the sample is biological material.

22. The method of claim 21, wherein the biological material is living tissue.

23. The method claim of 21, wherein the method further includes determining a physiological property of the biological material using the modulation characteristic.

24. The method of claim 21, wherein the method further includes determining a pathological property of the biological material using the modulation characteristic.

25. The method of claim 22, wherein the method further includes determining a physiological property of the living tissue using the modulation characteristic.

26. The method of claim 25, wherein the physiological property of the tissue is tissue oxygenation.

27. The method of claim 22, wherein the method further includes determining a pathological property of the tissue using the modulation characteristic.

28. The method of claim 27, wherein the pathological property of the tissue is the malignant condition of the tissue.

29. The method of claim 1, wherein either but not both of the distances is substantially zero.

30. A spectroscopic method of analyzing a sample, comprising:

irradiating a sample with radiation to produce return radiation from the sample, wherein the return radiation is modulated by the sample;

monitoring a first portion of the modulated return radiation at a first distance from the sample;

monitoring a second portion of the modulated return radiation at a second distance from the sample;

processing the first and second portions of the modulated return radiation to determine a modulation characteristic of the sample, wherein the return radiation is modulated by attenuation.

31. The method of claims 30, wherein the return radiation is attenuated by scattering.

32. The method of claim 30, wherein the return radiation is attenuated by absorption.

33. The method of claim 30, wherein the modulation characteristic of the sample is attenuation.

34. The method of claim 30, wherein the modulation characteristic of the sample is absorption.

35. The method of claim 34, wherein the method further includes determining transmittance.

36. The method of claim 30, wherein the modulation characteristic of the sample is optical rotation.

37. A spectroscopic method of analyzing a sample, comprising:

irradiating a sample with radiation to produce return radiation from the sample, wherein the return radiation is modulated by the sample;

monitoring a first portion of the modulated return radiation at a first distance from the sample;

monitoring a second portion of the modulated return radiation at a second distance from the sample;

processing the first and second portions of the modulated return radiation to determine a modulation characteristic of the sample;

wherein the sample is biological material;

wherein the method further includes determining a physiological property of the tissue using the modulation characteristic; and wherein the physiological property of the tissue is hypoxia.

38. A spectroscopic method for determining the oxygenation of a biological material, comprising:

irradiating a sample of a biological material with radiation to produce fluorescence from the sample, wherein the fluorescence is modulated by attenuation of the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence to determine the attenuation of the sample;

determining oxygenation of the sample using the attenuation of the sample.

39. A spectroscopic method for determining the oxygenation of a biological material, comprising:

irradiating a sample of a biological material with radiation to produce return radiation from the sample, wherein the return radiation is modulated by attenuation of the sample;

monitoring a first portion of the modulated return radiation at a first distance from the sample;

monitoring a second portion of the modulated return radiation at a second distance from the sample;

processing the first and second portions of the modulated return radiation to determine the attenuation of the sample;

determining oxygenation of the sample using the attenuation of the sample;

wherein the oxygenation of the sample is determined by comparing the attenuation of the sample to the attenuation of a sample having a known level of oxygenation.

40. A spectroscopic method for determining the concentration of hemoglobin in a biological material, comprising:

irradiating a sample of biological material with radiation to produce fluorescence from the sample, wherein the fluorescence is modulated by attenuation of the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence to determine the attenuation of the sample;

determining the concentration of hemoglobin in the sample using the attenuation of the sample.

41. A spectroscopic method for determining the concentration of hemoglobin in a biological material, comprising:

irradiating a sample of a biological material with radiation to produce return radiation from the sample, wherein the return radiation is modulated by attenuation of the sample;

monitoring a first portion of the modulated return radiation at a first distance from the sample;

monitoring a second portion of the modulated return radiation at a second distance from the sample;

determining the concentration hemoglobin in the sample using the attenuation of the sample;

wherein the concentration of hemoglobin is determined by comparing the attenuation of the sample to the attenuation of a sample having a known concentration of hemoglobin.

42. A method for determining a physiological characteristic of a biological material, comprising:

irradiating a sample of biological material with radiation to produce fluorescence from the sample, wherein the fluorescence is modulated by the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence, using a predictive model, to determine a physiological characteristic of the sample.

43. A method for determining a physiological characteristic of a biological material, comprising:

irradiating a sample of a biological material with radiation to produce return radiation from the sample, wherein the return radiation is modulated by the sample;

monitoring a first portion of the modulated return radiation at a first distance from the sample;

monitoring a second portion of the modulated return radiation at a second distance from the sample;

processing the first and second portions of the modulated return radiation, using a predictive model, to determine a physiological characteristic of the sample;

wherein the predictive model is a multivariate linear regression.

44. A method for determining a physiological characteristic of biological material, comprising:

irradiating a sample of biological material with radiation to produce fluorescence from the sample, wherein the fluorescence is modulated by the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence to determine a modulation characteristic of the sample;

processing the modulation characteristic using a predictive model to determine a physiological characteristic of the sample.

45. A method for determining a physiological characteristic of a biological material, comprising:

irradiating a sample of a biological material with radiation to produce return radiation from the sample, wherein the return radiation is modulated by the sample;

monitoring a first portion of the modulated return radiation at a first distance from the sample;

monitoring a second portion of the modulated return radiation at a second distance from the sample;

processing the first and second portions of the modulated return radiation, using a predictive model, to determine a physiological characteristic of the sample;

wherein the predictive model is a multicriteria associative memory classifier.

46. Apparatus for analyzing a sample, comprising:

a source adapted to emit radiation that is directed at a sample to produce fluorescence from the sample, wherein the fluorescence is modulated by the sample;

a first sensor adapted to monitor the fluorescence at a first distance from the sample and generate a first signal indicative of the intensity of the fluorescence;

a second sensor adapted to monitor the fluorescence at a second distance from the sample and generate a second signal indicative of the intensity of the fluorescence, the second distance being different from the first distance; and a processor associated with the first sensor and the second sensor and adapted to compare the first and second signals to determine a modulation characteristic of the sample.

47. The apparatus of claim 46, wherein fiber optics transmit the fluorescence to the sensors.

48. Apparatus for analyzing a sample, comprising:

a source adapted to emit radiation that is directed at a sample volume in a sample to produce fluorescence from the sample, such fluorescence including modulated fluorescence resulting from modulation by the sample;

a first sensor adapted to monitor the fluorescence at a first distance from the sample volume and generate a first signal indicative of the intensity of the fluorescence;

a second sensor adapted to monitor the fluorescence at a second distance from the sample volume and generate a second signal indicative of the intensity of the fluorescence, the second distance being different from the first distance;

a processor associated with the first sensor and the second sensor and adapted to compare the first and second signals to determine a modulation characteristic of the sample.

49. Apparatus for determining a modulation characteristic of a biological material, comprising:

a source adapted to emit excitation light;

a first waveguide disposed a first distance from the sample adapted to transmit the excitation light from the light source to the biological material to cause the biological material to produce fluorescence and adapted to collect a first portion of the fluorescence;

a first sensor, associated with the first waveguide, adapted to measure the intensity of the first portion of the fluorescence and generate a first signal indicative of the intensity of the first portion of the fluorescence;

a second waveguide disposed at a second distance from the sample adapted to collect a second portion of the fluorescence, the second distance being different from the first distance;

a second sensor, associated with the second waveguide, adapted to measure the intensity of the second portion of the fluorescence and generate a second signal indicative of the intensity of the second portion of the fluorescence;

a processor adapted to compare the first and second signals to determine a modulation characteristic of the biological material.

50. Apparatus for analyzing a sample, comprising:

a source adapted to emit radiation that is directed at a sample volume in a sample to produce fluorescence from the sample, such fluorescence including modulated fluorescence resulting from modulation by the sample;

a first sensor, displaced by a first distance from the sample volume adapted to monitor the fluorescence and generate a first signal indicative of the intensity of the fluorescence; and a second sensor, displaced by a second distance from the sample volume adapted to monitor the fluorescence and generate a second signal indicative of the intensity of fluorescence, the second distance being different from the first distance;

a processor associated with the first sensor and the second sensor and adapted to compare the first and second signals to determine a physiological property of the sample.

51. Apparatus for determining a physiological property of biological material, comprising:

a source adapted to emit excitation light;

a first waveguide disposed a first distance from the sample adapted to transmit the excitation light from the light source to the biological material to cause the biological material to produce fluorescence and adapted to collect a first portion of the fluorescence;

a first sensor, associated with the first waveguide, for measuring the intensity of the first portion of the fluorescence and generating a first signal representative of the intensity of the first portion;

a second waveguide disposed at a second distance from the sample adapted to collect a second portion of the fluorescence, the second distance being different from the first distance;

a second sensor, associated with the first waveguide, for measuring the intensity of the second portion of the fluorescence and generating a second signal representative of the intensity of the second portion;

a processor adapted to compare the first and second signals to determine a physiological property of the biological material.

52. A spectroscopic method of analyzing a sample, comprising:

irradiating a sample with radiation to produce fluorescence from the sample, wherein the fluorescence is modulated by the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence to determine a modulation characteristic of the sample;

wherein the sample is biological material;

wherein the method further includes determining a physiological property of the tissue using the modulation characteristic; and wherein the physiological property of the tissue is ischemia.

53. A method for determining a physiological characteristic of a biological material, comprising:

irradiating a sample of a biological material with radiation to produce fluorescence from the sample, wherein the fluorescence is modulated by the sample;

monitoring a first portion of the modulated fluorescence at a first distance from the sample;

monitoring a second portion of the modulated fluorescence at a second distance from the sample, the second distance being different from the first distance;

comparing the first and second portions of the modulated fluorescence, using a predictive model, to determine a physiological characteristic of the sample;

wherein the predictive model is multivariate.

54. A spectroscopic method of analyzing a sample, comprising:

irradiating a sample with radiation to produce fluorescence from the sample, wherein the fluorescence is modulated by the sample;

monitoring a first portion of the modulated fluorescence at a first angle from the sample monitoring a second portion of the modulated fluorescence at a second angle from the sample comparing the first and second portions of the modulated fluorescence to determine a modulation characteristic of the sample.

* * * * *